United States Patent [19]
Lenox et al.

[11] Patent Number: 6,056,689
[45] Date of Patent: May 2, 2000

[54] DEVICE AND METHOD FOR LOCALIZED HEART MOTION DAMPENING AT A CARDIAC SURGICAL SITE

[75] Inventors: Linda Kathleen Lenox, Boulder; Carl A. Schmidt, Denver, both of Colo.

[73] Assignee: Lenox - MacLaren, Boulder, Colo.

[21] Appl. No.: 09/133,637

[22] Filed: Aug. 13, 1998

Related U.S. Application Data

[63] Continuation-in-part of application No. 08/787,343, Jan. 25, 1997, Pat. No. 5,865,731.

[51] Int. Cl.⁷ .................................................... A61B 17/00
[52] U.S. Cl. ............................ 600/217; 600/210; 600/235
[58] Field of Search ..................................... 600/201, 204, 600/210, 217, 235; 128/898

[56] References Cited

U.S. PATENT DOCUMENTS

| | | | |
|---|---|---|---|
| 5,836,311 | 11/1998 | Borst et al. | ............................ 600/201 X |
| 5,875,782 | 3/1999 | Ferrari et al. | ........................ 600/235 X |
| 5,894,843 | 4/1999 | Benetti et al. | ........................ 600/201 X |
| 5,921,979 | 7/1999 | Kovac et al. | ................................. 606/1 |

FOREIGN PATENT DOCUMENTS

| | | | |
|---|---|---|---|
| 0 791 330 A2 | 8/1997 | European Pat. Off. | ............... 600/201 |
| 98/17182 | 4/1998 | WIPO | .................................... 600/201 |

*Primary Examiner*—Jeffrey A. Smith
*Attorney, Agent, or Firm*—Sheridan Ross P.C.

[57] ABSTRACT

A device and method are disclosed for dampening the heart motions of a patient's beating heart in a local area of a desired surgical site. The heart motion dampening is provided by a ring-like structure having prongs attached thereto, wherein the prongs engage or penetrate heart tissue in a manner effective for both anchoring the device of the present invention and for transmitting heart motion dampening resistive forces to the area about the surgical site so that the patient's heart is substantially still at the surgical site.

15 Claims, 23 Drawing Sheets

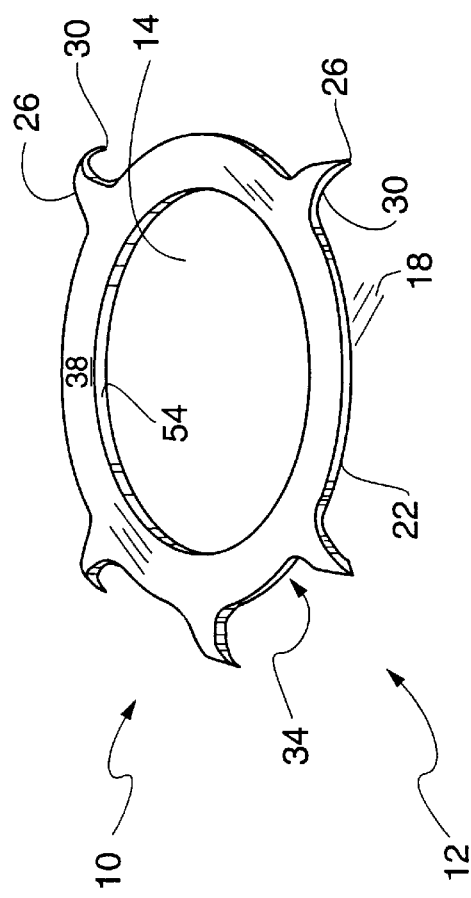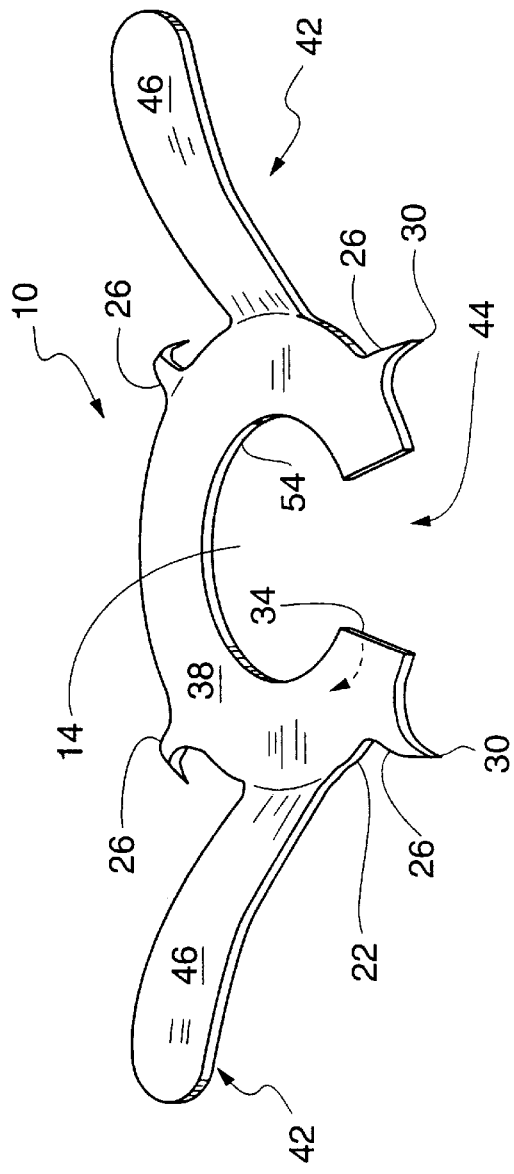

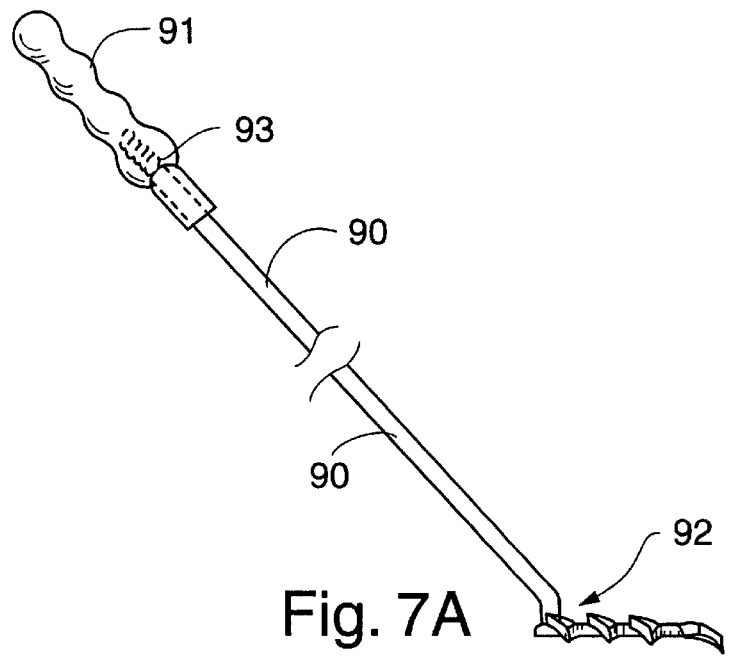
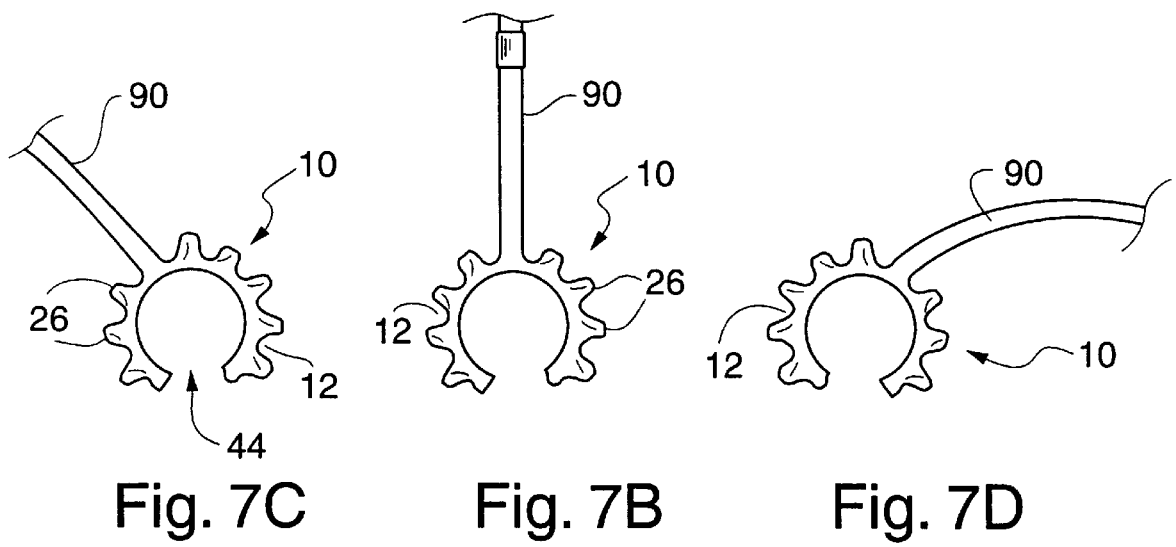
Fig. 7A
Fig. 7C  Fig. 7B  Fig. 7D

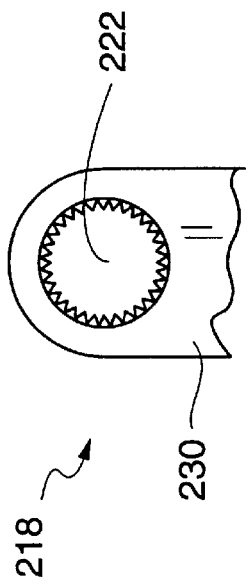
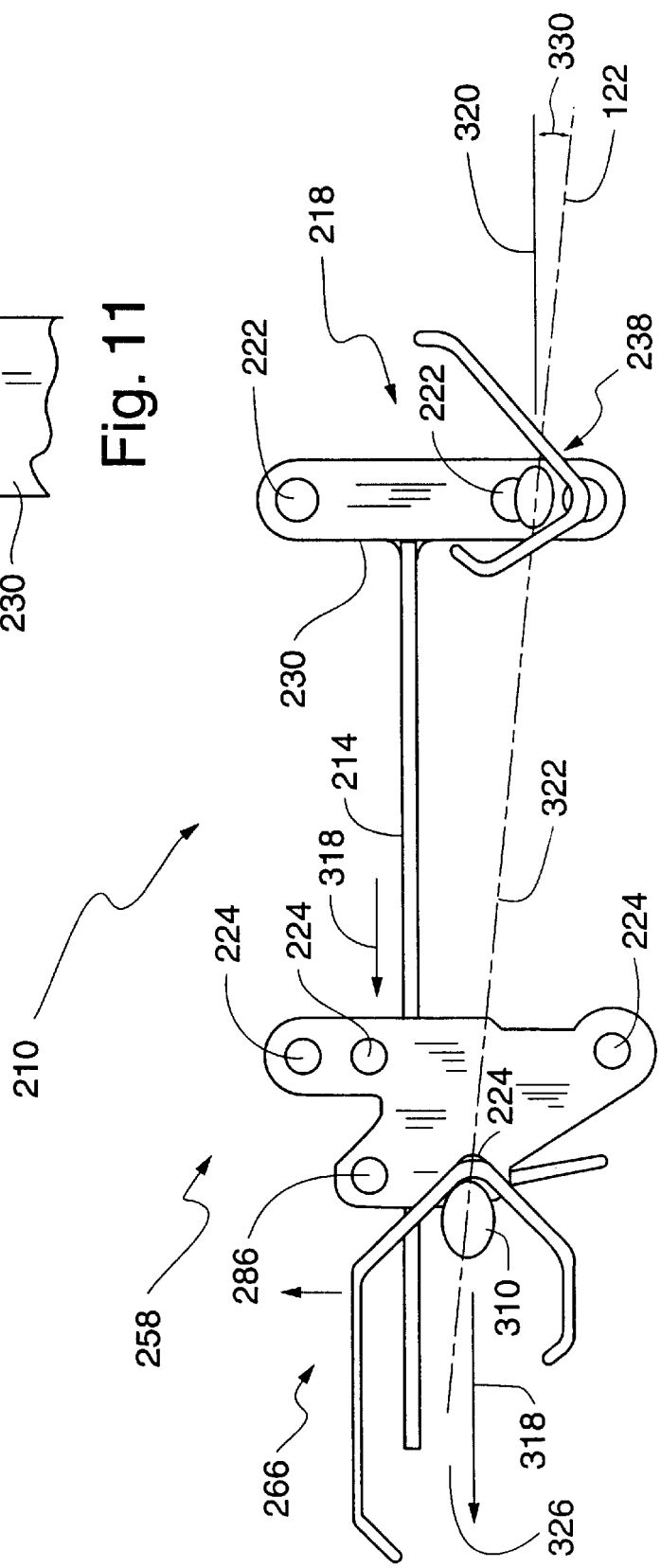

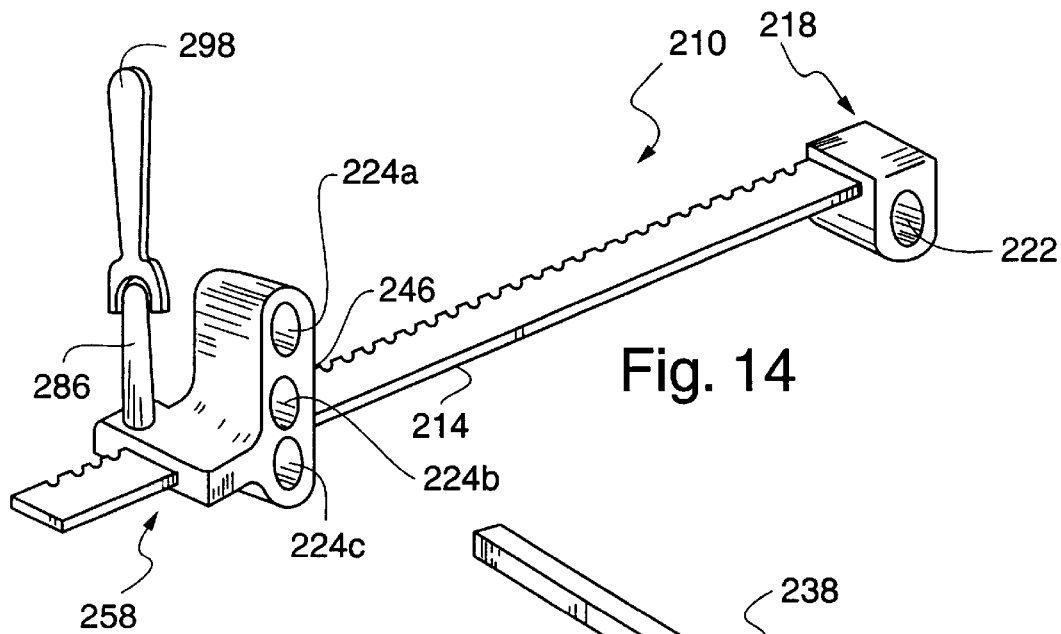
Fig. 14
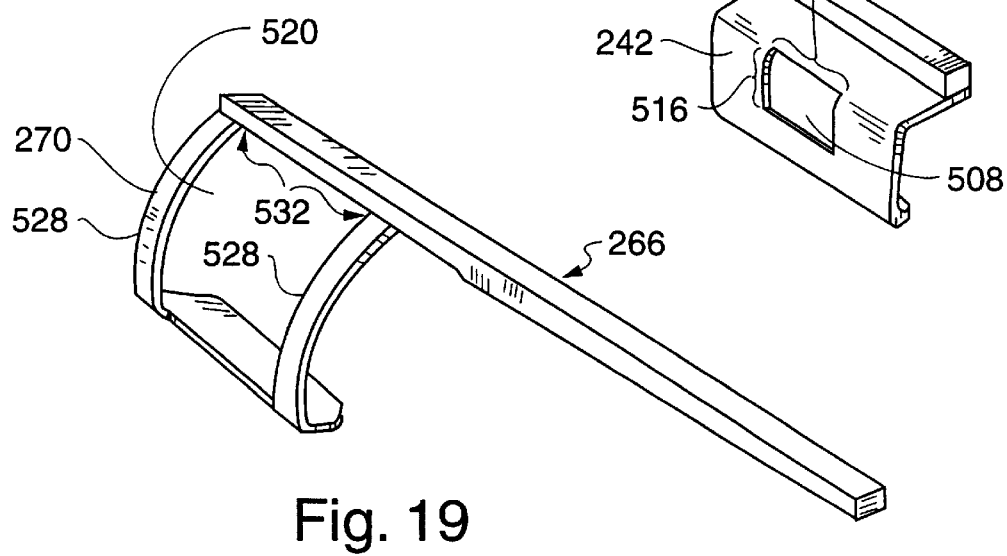
Fig. 18
Fig. 19

DEVICE AND METHOD FOR LOCALIZED HEART MOTION DAMPENING AT A CARDIAC SURGICAL SITE

CROSS REFERENCE TO RELATED APPLICATIONS

The present application is a continuation-in-part application of U.S. application Ser. No. 08/787,343, filed Jan. 25, 1997, now U.S. Pat. No. 5,865,731, entitled "SURGICAL RETRACTOR HAVING VARIABLE POSITION RETRACTOR BLADES." The present application also claims priority from U.S. Provisional Application Ser. No. 60/055,738, filed Aug. 13, 1997.

FIELD OF THE INVENTION

The present invention relates to a heart motion dampening device and method for use in a cardiac surgical procedure, and more particularly, relates to a heart motion dampening device having heart tissue engaging prongs that penetrate the heart tissue.

BACKGROUND OF THE INVENTION

During a cardiac surgical procedure, it is necessary to perform surgical procedures upon the heart while the heart is beating. The rhythmic beating of the heart generates motions that make it difficult for surgical procedures to be carried out directly upon the heart. In particular, during heart bypass operations, it is necessary to attach bypass arteries or veins to the beating heart by, for example, suturing. It can be extremely difficult, however, to perform such an attachment effectively when the heart is beating.

Accordingly, it would be advantageous to have an effective surgical device and method for dampening the heart motion in a local area on the heart where a surgical procedure is to be performed.

SUMMARY OF THE INVENTION

The present invention is directed to a surgical device and method for dampening the rhythmic motions of a patient's heart during a cardiac surgical procedure. In particular, the present invention dampens the motions of the patient's beating heart in a localized area on the surface of the heart where a surgical procedure is to be performed. More particularly, the present invention provides a novel technique for locally dampening heart motions by providing a structure, preferably ring-like in shape, having prongs or projections that grip the surface tissue of the heart to thereby anchor the structure directly to the heart. Upon applying a resistive force or forces to the heart motion via, for example, the ring-like structure, an interior opening in a ring-like structure provides access to the surgical site without the typical heart motions complicating the surgical technique being performed thereon.

A further aspect of certain embodiments of the present invention involves the provision of attachments or flanges on the present heart stabilizing device for transmitting resistive forces to the beating heart, thus dampening the heart motion. Such flanges may be used for manually applying pressure to the present invention so that it maintains a predetermined position on the patient's heart. Alternatively, in other embodiments of the flanges, they may be grasped by surgical equipment (such as clamps) and thereby held in place providing the necessary resistive or dampening forces. Alternatively, the heart dampening device of the present invention may be held in place by an assembly attached to a surgical retractor.

Additionally, other heart motion dampening techniques and materials may also be incorporated into the present invention. In particular, elastic or resilient foams or gels may be used in combination with the prongs for dampening the heart motions. That is, in one embodiment, by providing such elastic or resilient materials in an area extending beyond the ring-like structure, such resilient materials may be used for partially dampening the heart motions in a wider area than the ring-like structure so that the sites where the prongs penetrate the heart tissue do not experience all the stress induced by the resistive or dampening forces that are transmitted through the prongs.

It is a further aspect of the present invention that the ring-like structure need not entirely enclose its interior opening. That is, at least a portion of the interior opening may be accessible from beyond the outer perimeter of the ring-like structure through a predetermined opening so that, for example, a surgical technique requiring access to both the interior opening of the ring-like structure and heart tissue in an area outside of the interior opening may be accessed without a portion of the ring-like structure intervening.

Other features and benefits of the present invention will become apparent from the detailed description with the accompanying figures contained hereinafter.

BRIEF DESCRIPTION OF THE DRAWINGS

FIG. 1 is a first embodiment of the present invention wherein the prongs 26 are attached to the ring-like structure 12 on an outer perimeter.

FIG. 2 is another embodiment of the present invention wherein flanges 42 are included for applying resistive or heart motion dampening forces to the ring-like structure 12.

FIGS. 7A, 7B, 7C, and 7D illustrate embodiments of the present invention wherein the shaft 90 is configured in three different ways in relation to the ring-like structure 12.

FIG. 11 is an exemplary view of a bore 222 of the surgical retractor 210, wherein the bore is viewed face on from the surface 230.

FIG. 12 illustrates the use of the retractor 210 in spreading two adjacent ribs of a patient, wherein this figure illustrates the forces induced on the ribs by the retractor 210.

FIG. 14 is another alternative embodiment of the present invention (without the retractor levers being shown).

FIGS. 18 and 19 are embodiments of the retractor levers useful in cardiac valve replacement surgery.

DETAILED DESCRIPTION OF A PREFERRED EMBODIMENT OF THE INVENTION

Figure 3:
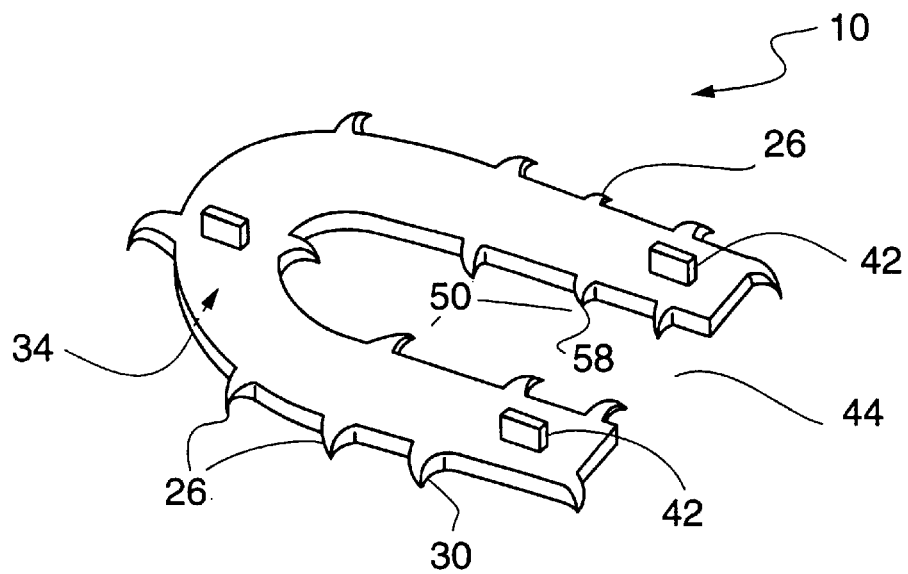
FIG. 3 illustrates a further embodiment of the present invention wherein the flanges 42 may be grasped by various surgical tools and/or surgical retractor connection assemblies for applying the forces necessary to locally dampen the patient's heart motions. Additionally, the present embodiment also illustrates that heart tissue engaging prongs may also be positioned about an inner boundary of the interior opening 14.

FIG. 1 presents one embodiment of the heart motion dampening device 10 of the present invention. This device is essentially a ring-like structure 12 that has the general shape of a disc with an interior opening. Other shapes, for example, rectangular, oval, triangular, etc., are also within the scope of the present invention. The thickness is typically less than approximately 2 mm. The interior opening 14 is intended to provide access to a desired surgical site on a beating heart. The area circumscribed by the structure 12 can vary but should be of sufficient size to permit easy access to the surgical site (e.g., between about 5 and about 30 mm, more preferably at least about 15 mm and most preferably at least about 20 mm). On the outer perimeter 22 of the ring-like structure 12 there are a plurality of heart tissue engaging prongs 26 spaced around this outer perimeter. In one embodiment, each prong 26 is preferably curved or slanted so that the points 30 will contact and potentially attach to a substantially planar surface or portion of tissue that comes into contact with the underside or bottom surface 34 that is opposite the top surface 38 of the device 10. Thus, when the device 10 is placed upon a beating heart with the underside 34 against the heart tissue and the top surface 38 facing away from this tissue, then by applying a force or pressure to the device 10, generally directed normal to the top surface 38, the device 10 becomes anchored on the heart tissue surface. Subsequently, by continuing to apply such a force or pressure along with resistance forces to counter the beating of the heart, the device 10 and the heart tissue exposed through the interior opening 14 becomes substantially stable or still. Thus, due to the anchoring and the thinness of the thickness 18, a surgical procedure such as suturing a bypass artery or vein to the heart can be performed more efficiently and safely.

However, note that various embodiments for anchoring the device 10 are within the scope of the present invention. That is, any configuration of serrations, prongs, points, edges, undulations and convolutions in the bottom surface 34, or, its edges, boundaries or perimeters that inhibit slippage of the device 10 from its desired position is within the scope of the present invention. Thus, although simple prongs or edges are illustrated in many of the figures, one skilled in the art can readily envision other configurations. Examples of such configurations are shown in FIGS. 23A–23F. Accordingly, the embodiments of the device 10 shown in various of the FIGS. 1 through 22 are only representative.

FIG. 2 illustrates a second embodiment of the present invention (having the same numeric labels as in FIG. 1 for similar features), wherein this embodiment additionally includes hold down attachments or flanges 42 for assisting a surgeon or other surgical team member in manually applying force to the device 10 for dampening the heart motion in the area exposed by interior opening 14. For instance, a surgical team member may press against the flange surfaces 46 with his/her fingers to provide the necessary dampening resistance so that the surgeon can perform a localized surgical procedure within the interior opening 14. This embodiment reduces or eliminates the need for surgical devices, such as surgical pliers, to be used to hold the device 10 in place. Note that the present embodiment additionally includes an opening 44 providing access to the interior opening 14, wherein the ring-like structure is substantially, but not completely closed. Further, note that the opening 44 may be advantageous in certain surgical procedures wherein, for example, bypass tissue such as a bypass artery or vein is preferred to lay flat against the heart without any intervening objects or surgical devices. Accordingly, such tissue may be laid upon the heart in the interior opening 14 and additionally traverse the opening 44. Thus, the artery or vein can be sutured to the heart and subsequently device 10 can be easily extracted without, for example, threading the artery or vein through a completely enclosed interior opening 14. Moreover, the opening 14 in the structure 12 is preferably of a size that provides enough space for a mammary artery graft to be laid upon the heart and sutured in the interior opening 14 (e.g., about 10 to 30 mm).

In FIG. 3, a third embodiment of the present invention is provided. In this embodiment, in addition to the heart tissue engaging prongs 26 on the outer perimeter 22, there are prongs 50 provided about the inner boundary 54 of the interior opening 14. As with the prongs 26, the prongs 50 are also directed so that their points 58 engage the heart tissue provided substantially adjacent to underside 34. Note that the present embodiment may provide additional anchoring points engaging the surface of the heart tissue and thereby provide greater stabilization of the area exposed by the interior opening 14. Additionally, note that the present embodiment shows that the interior opening 14 can be shaped oblongly instead of circularly. Thus, in surgical procedures where it is advantageous to dampen heart motion along a relatively straight path, the present embodiment may be preferred. Of course curved variations of the interior openings are also possible, wherein (a) the device 10 is curved to fit contours of the heart and/or curved to fit the contours of a particular surgical path.

Further, note that a second embodiment of the hold down attachments or flanges 42 is provided in the embodiment of FIG. 3, wherein these flanges project substantially normal to the top surface 38 and are shaped so that, for example, each can be easily grasped by a surgical instrument such as a surgical clamp or pliers, thereby allowing one or more surgical team members to apply resistance forces to the heart dampening device 10 via the one or more surgical instruments grasping the flanges 42. Accordingly, this embodiment may provide greater access by the surgeon to the heart tissue exposed in the interior opening 14.

Figure 4:
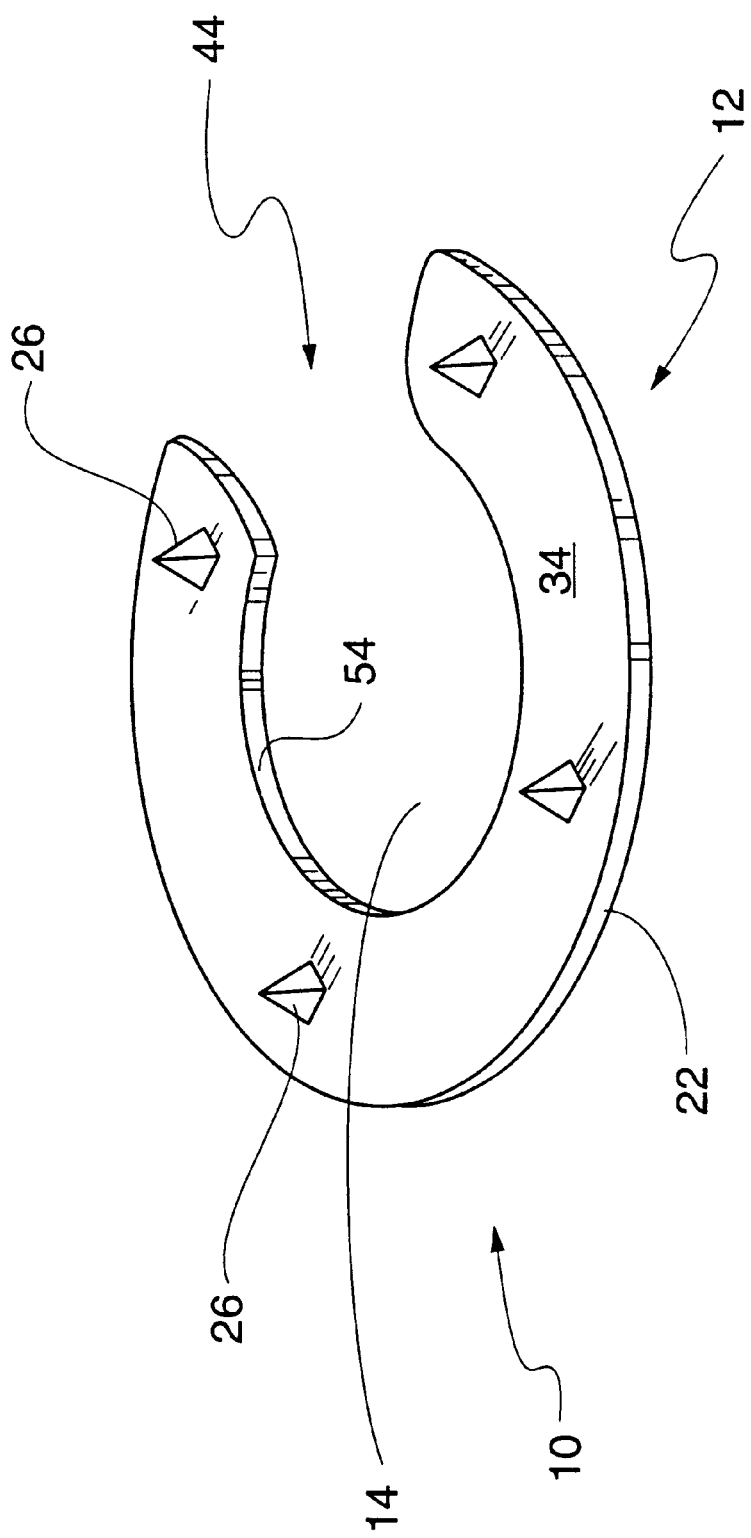
FIG. 4 is yet another embodiment of the present invention wherein an additional structure 80 is provided beyond the ring-like structure 12 for partially dampening the patient's heart motions by, for example, elastic or resilient materials.

FIG. 4 illustrates yet another embodiment of the present invention wherein the ring-like structure 12 is surrounded by an additional structure 80 having a further heart motion dampening effect. In particular, the additional structure 80 may have heart motion dampening elastic compounds such as a foam or gel in, for example heart contact areas 82, for providing further resistance to the motion of the heart, thereby at least partially dampening the motions transmitted to the ring-like structure 12. Also, the additional structure 80 may have: (a) a frame 86 that is flexible but substantially stiff when exposed to the forces of a beating heart, and (b) heart tissue contacting surfaces (particularly those surfaces from contact areas 82,) that resist slippage. Moreover, this embodiment also shows that the device 10 includes an applicator shaft or wire 90 attached to the ring-like structure 12 at one end and to a handle 91 at the other end. Note that the shaft 90 can be of any appropriate length for applying locally dampening resistance to heart motion. Also, the shaft 90 may be held manually or by a mechanical assembly such that the shaft 90 extends from outside the patient and through, for example, the tunnel-like body cavities produced during surgical procedures having restricted incision openings (i.e., also known as "mini-surgery").

Figure 5:
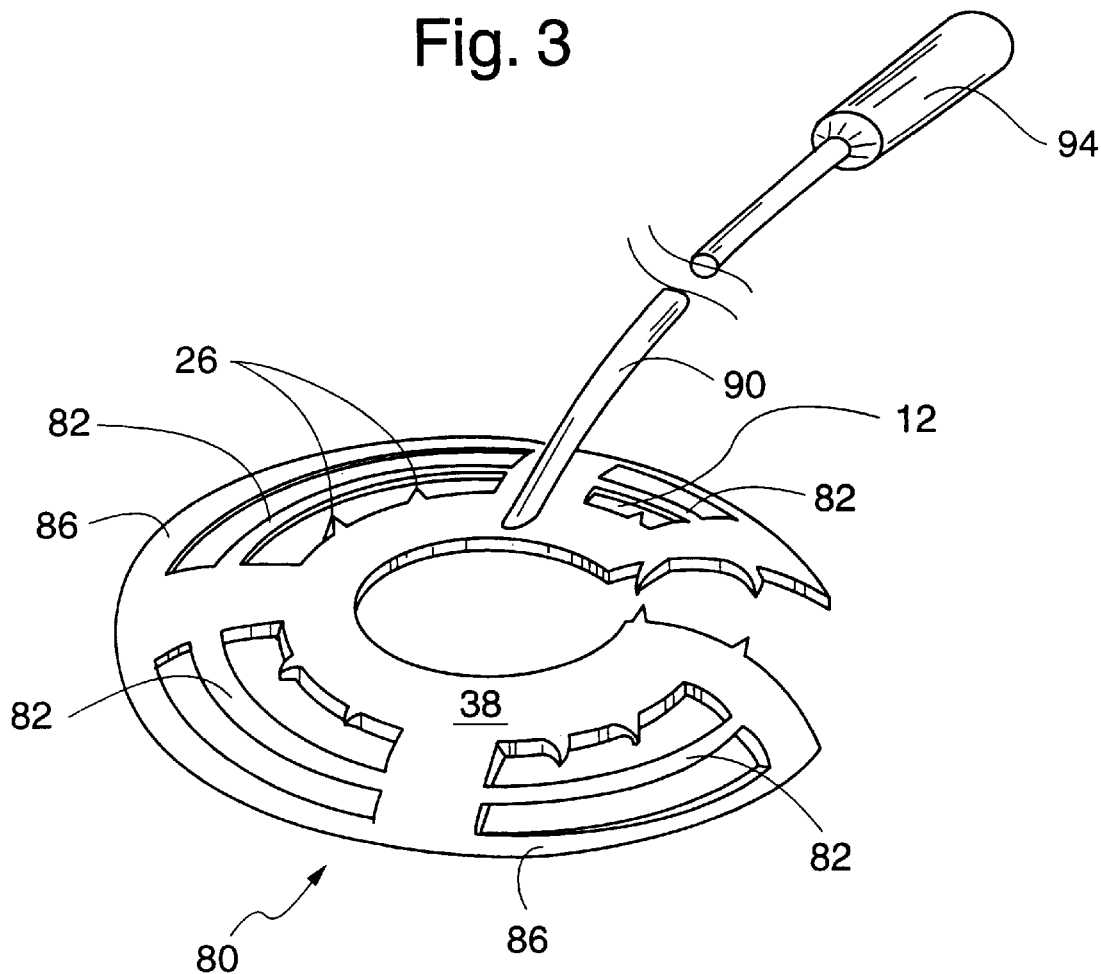
FIG. 5 is another embodiment of the present invention wherein the ring-like structure 12 is not entirely closed and the prongs are on the underside of the ring-like structure.

FIG. 5 presents yet another embodiment of the present invention wherein the heart tissue engaging prongs or projections 26 are provided on the underside 34 instead of, or in addition to, any prongs on the outer perimeter 22 and/or the inner boundary 54.

Figure 6:
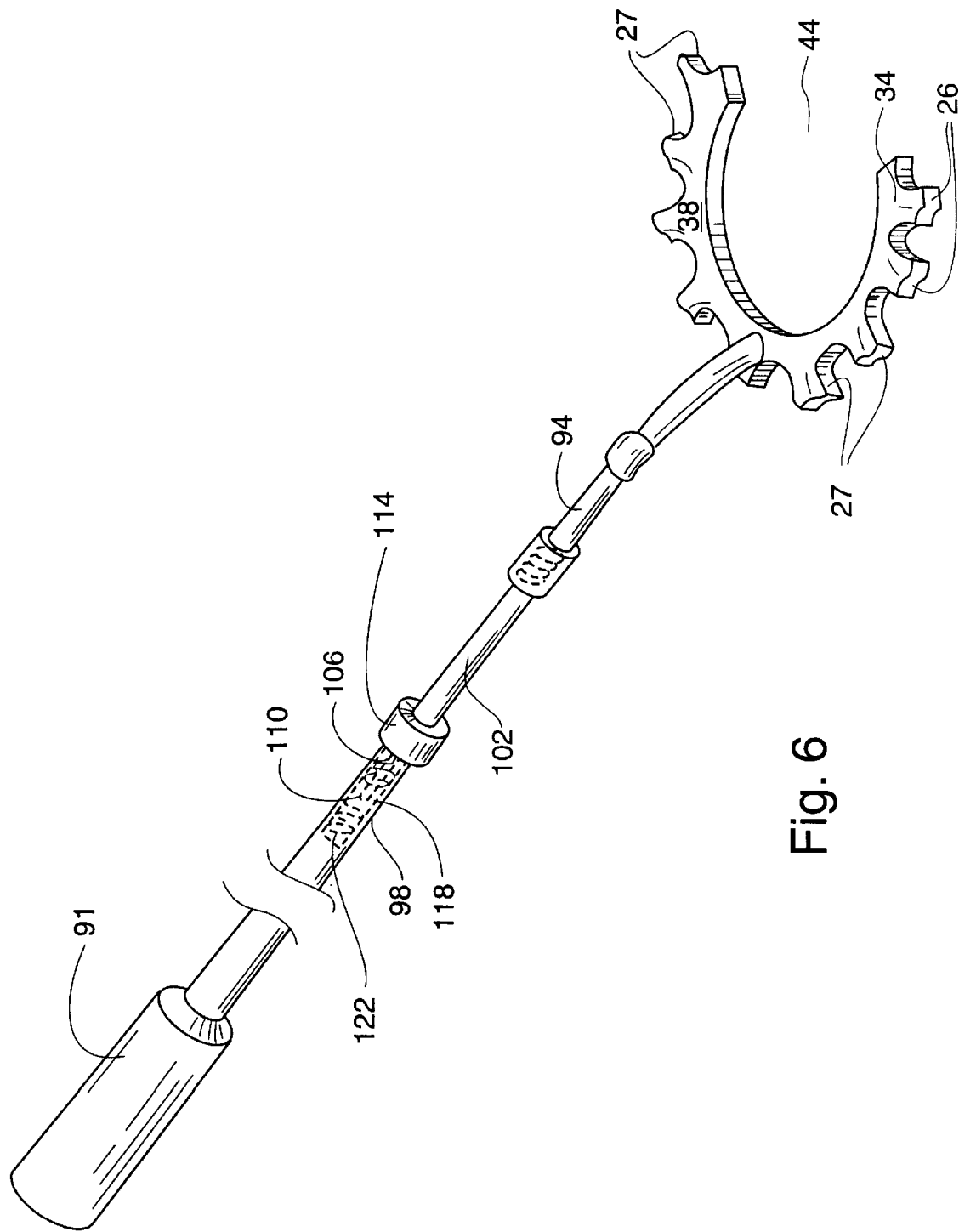
FIG. 6 is another embodiment of the present invention wherein the shaft 90 for holding the ring-like structure in place is both extendable and includes spring loaded telescoping portions.

FIG. 6 illustrates a further embodiment of the present invention, wherein the device 10 has a star-shaped ring-like structure 12 with the prongs 26 having rounded or truncated tips instead of points 30. Accordingly, to provide the heart grasping functionality of the points 30, each prong 26 of the present embodiment has a sharp edge 27 that is angled toward the heart and that extends slightly further toward the heart than the bottom surface 34. Additionally, the device also has a shaft 90 attached to the ring-like structure 12 substantially opposite the opening 44. Note that the shaft 90 of the present embodiment can have its length varied by attaching shaft attachments 94 that, for example, threadably attach to other portions of the shaft. Additionally, note that the shaft 90 may also include telescoping spring loaded shaft portions 98 and 102, wherein shaft portion 102 telescopes within shaft portion 98. More particularly, shaft portion 102 includes at least one key or protrusion 106 that projects outwardly from the generally cylindrical shape of the shaft portion 102, and this key(s) is retained within a key slot 110 by a retaining member 114 that is, for example, threaded onto the end of shaft portion 98 adjacent shaft portion 102. Moreover, the shaft portion 102 telescopes into a chamber 118 of shaft portion 98 while the key(s) 106 maintain the two shaft portions in proper alignment to prevent binding. Further, the chamber 118 includes a compression spring 122 for biasing the shaft portion 102 against movement into the chamber 118. Thus, the telescoping, spring loaded shaft portions 98 and 102 facilitate providing a more constant pressure between the ring-like structure 12 and the beating heart. Further, the present configuration of the shaft 90 allows some movement of the heart in, for example, directions substantially normal to the top surface 38 while at the same time substantially inhibiting lateral motions that have a directional component substantially parallel to the top surface 38.

FIG. 7A presents a side view of an embodiment of the present invention similar to the embodiment of FIG. 6. However, in the embodiment of FIG. 7A, the shaft 90 is a .097 inch flexible stainless steel wire that is manually bendable by a surgeon during a surgical procedure. Thus, the surgeon may provide various arcs or curves to the shaft 90, particularly in the portion of the shaft between the shaft angled portion 92 (angled typically in the range of 30° to 60°) and the handle 91. Moreover, in the present embodiment, the handle 91 is threaded onto the thread portion 93 of the shaft 90 and a nut 95 may be used to secure the handle onto the shaft.

FIGS. 7B, 7C and 7D present top views illustrating various configurations of the shaft 90 attached to the ring-like structure 12.

Figure 8A:
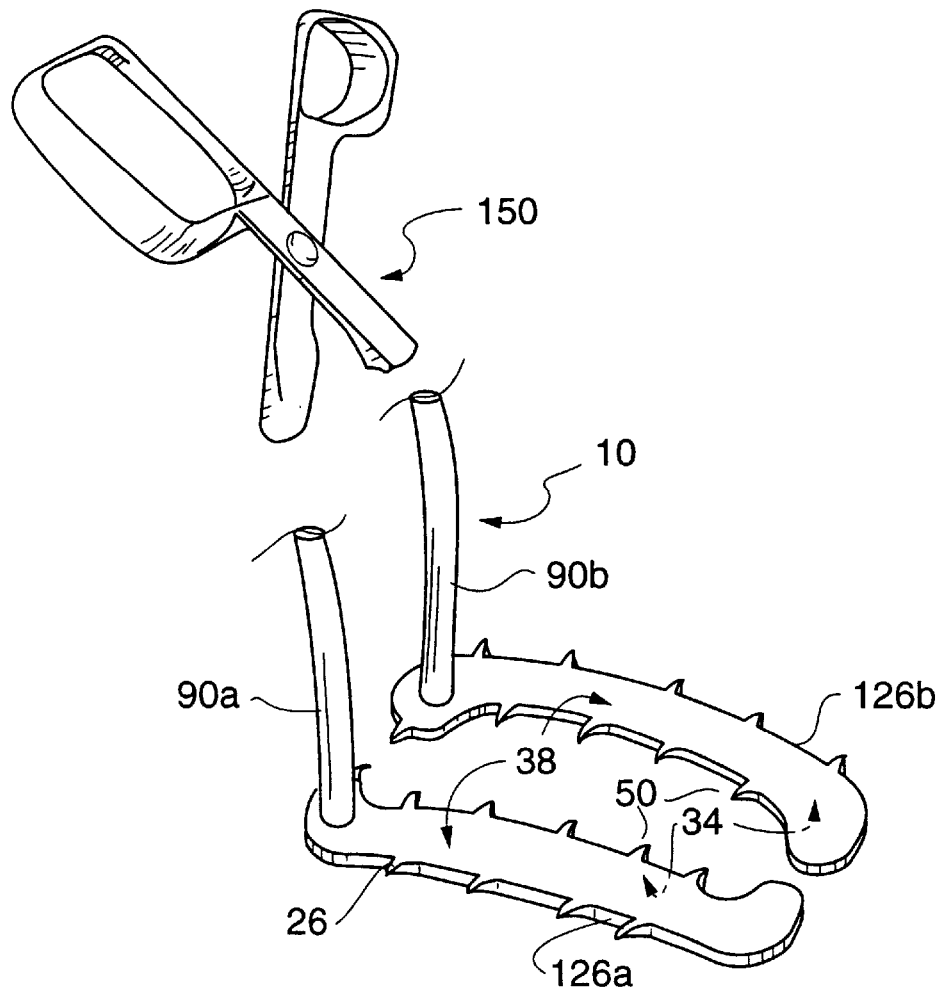
FIGS. 8A, 8B and 8C illustrate another embodiment of the present invention, wherein two disconnected ring halves 126a and 126b are used for grasping heart tissue therebetween.
Figure 8B:
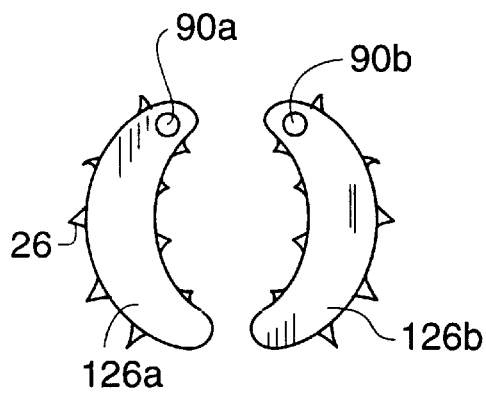
Figure 8C:
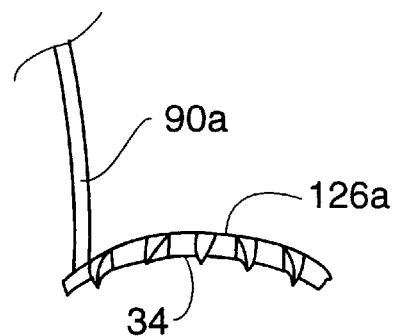

FIGS. 8A, 8B and 8C present yet another embodiment of the heart dampening device 10. In the embodiment of these figures, the ring-like structure 12 is decomposed into two curved ring halves 126a and 126b that may be substantially mirror images of one another. Further, each of the ring halves 126 has an attached shaft 90 and these shafts are attached to one another in scissor-like fashion at attachment point 150. Thus, the present embodiment may be used for grasping a portion of the patient's heart and holding the heart tissue between the ring halves 126a and 126b still while a surgeon performs a surgical procedure thereon. Note that in the present embodiment, instead of applying forces or pressures substantially normal to the top surface 38, (as in many of the previous embodiments above), the forces applied by this embodiment may be substantially lateral or parallel to both the top surface 38 and the surface of the heart whose tissue is being grasped by the prongs 50 and/or 26. Moreover, the present embodiment can provide further advantages in that the lateral forces used in grasping the heart can also cause the tissue between the ring halves 126a and 126b to bulge somewhat so that the surgeon is provided with better access to the heart tissue therebetween. Further, such grasping allows the heart to be lifted instead of pressed upon as in the other embodiments. Also note that, as best shown in FIG. 8C, the ring halves 126a and 126b are curved so that the bottom surface 34 is curved with a contour that generally conforms to the curvature of the patient's heart. Thus, the prongs 26 distributed along the ring halves 126 more evenly grab and distribute heart dampening pressures to the heart tissue therebetween.

Figure 9:
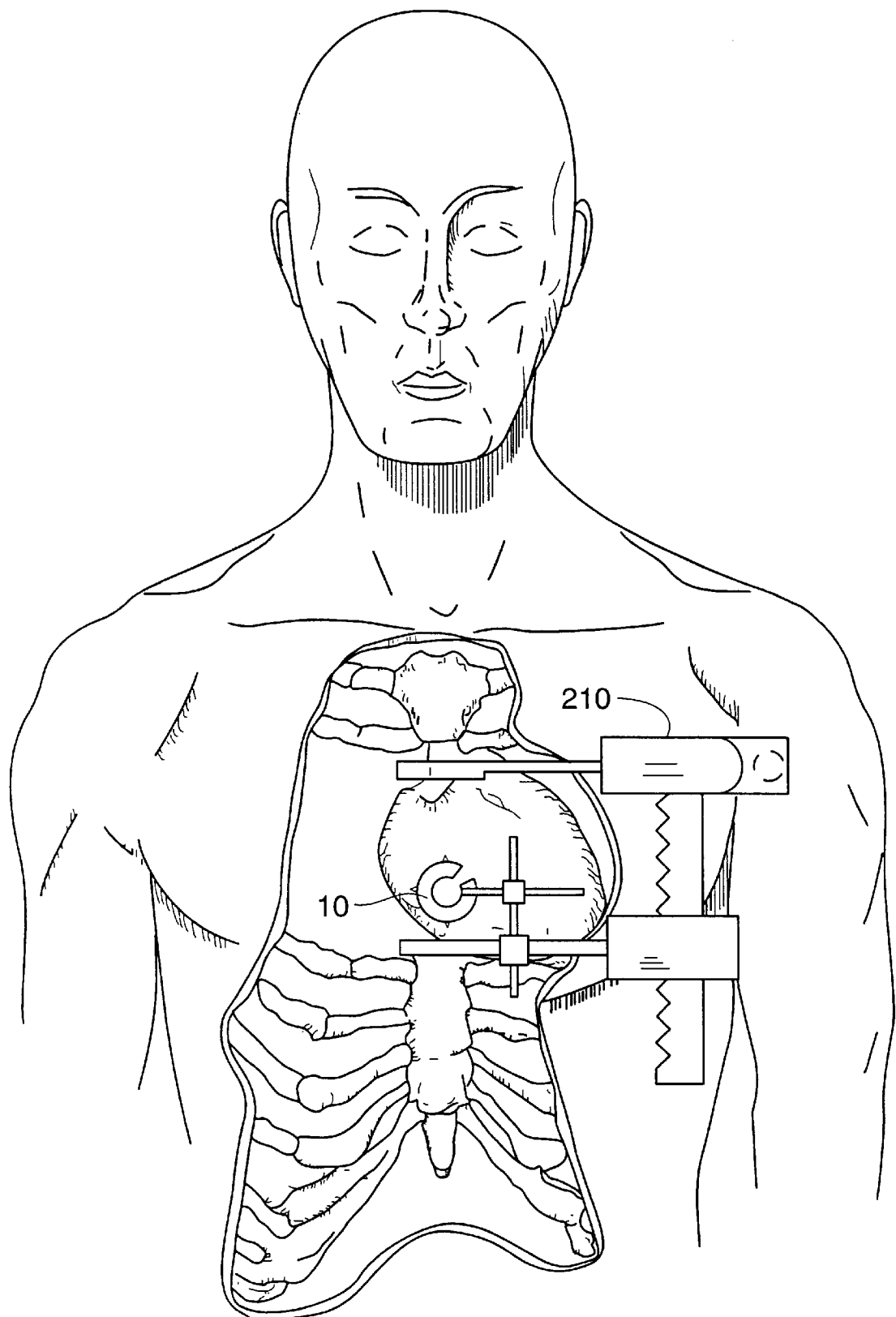
FIG. 9 illustrates the use of the heart motion dampening device of the present invention during a cardiac surgical procedure, wherein the present invention is pressed against the patient's heart using a surgical retractor assembly 58 attached to one of the retractor levers.

FIG. 9 illustrates the use of an embodiment of the present invention having flanges 42 (such as the flanges of FIG. 3) capable of being gripped, wherein the flanges 42 are grasped (or otherwise connected to) a mechanical assembly 58 for providing the necessary heart dampening forces to the device 10. In the present figure, the mechanical assembly 58 is attached to the device 10 via a flange 42 (not visible) substantially at location 62. Additionally, the assembly 58 is connected to a surgical retractor lever 66 of surgical retractor 70. As one skilled in the art will understand, the assembly 58 includes adjustable components 74, each having perpendicular bores therethrough for adjusting the position and orientation of each rod or lever provided within the bores so that the orientation of the device 10 can be easily adjusted to substantially conform to the general contour of the heart in the location of the desired surgical site. In one embodiment, the device is attached to a midcab retractor that has a design which permits opposing blades to be manipulated so as to create, for example, a cavity in a patient's chest. Such a retractor is described hereinbelow.

Figure 10:
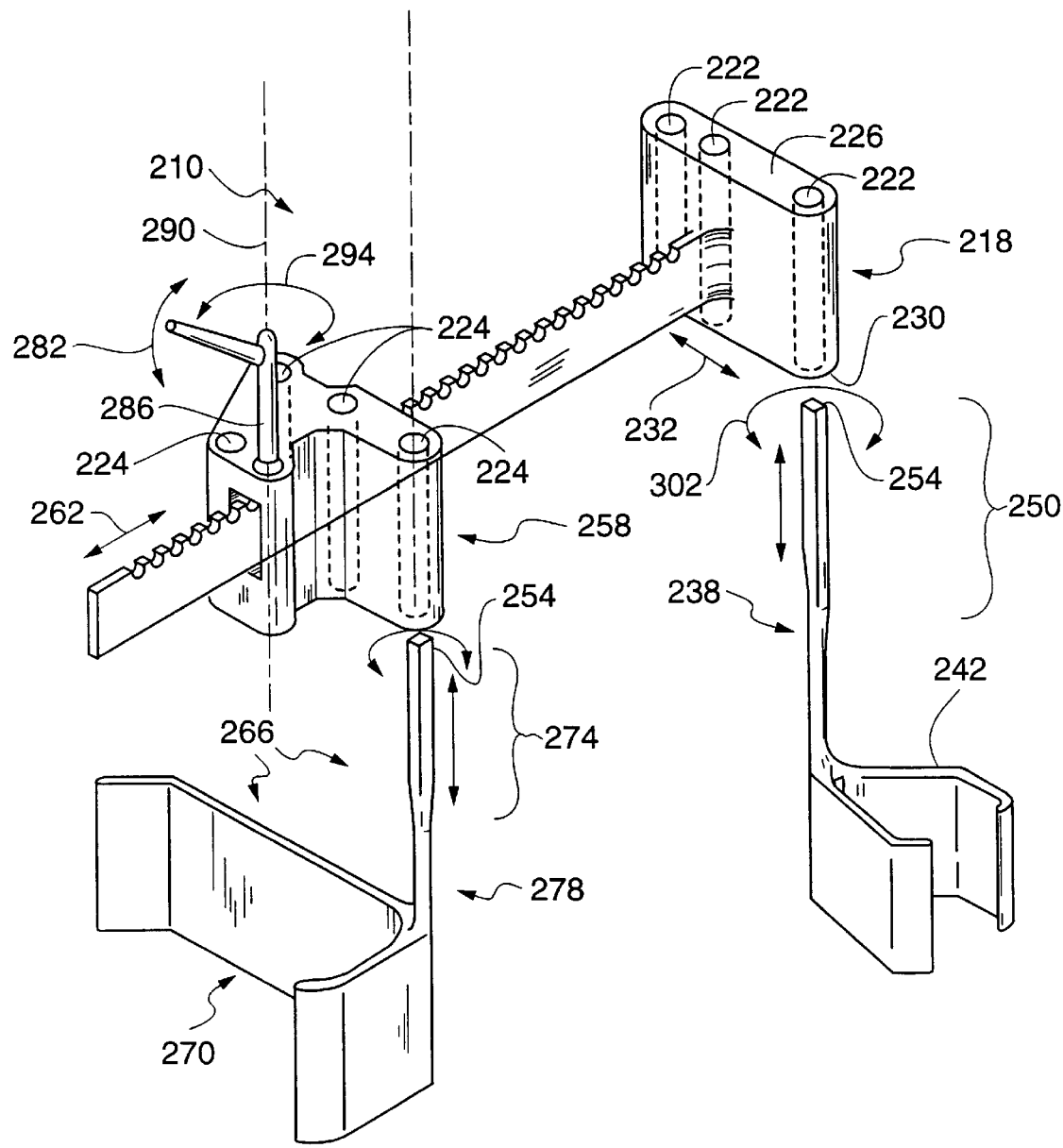
FIG. 10 is an embodiment of a retractor 210 to which the heart motion dampening device 10 of the present invention may be attached.
Figure 13:
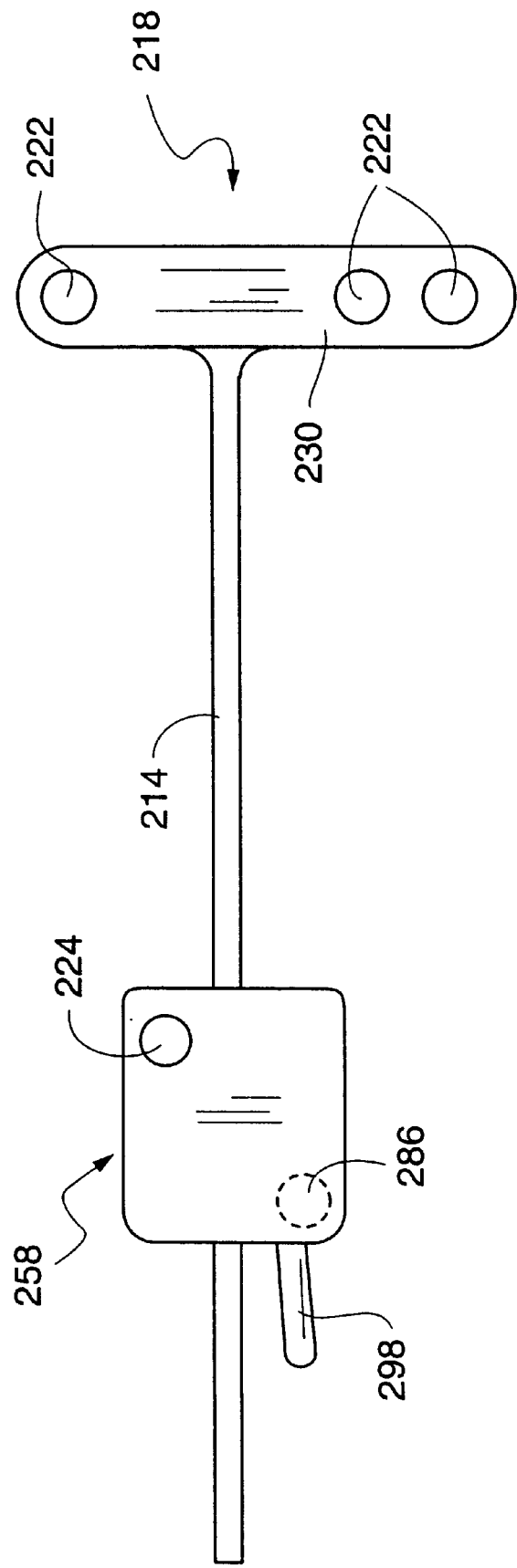
FIG. 13 illustrates an alternative embodiment of the surgical retractor 210 (without retractor levers being shown), wherein the movable head 258 has only a single bore 224.

In FIG. 10, an embodiment of a surgical retractor 210 to which the device 10 may be attached. The retractor 210 includes a toothed crossbar 214 fixedly attached to a stationary head 218 at one end of the crossbar 214. The stationary head 218 is preferably attached to the crossbar in an offset manner as is best shown in FIG. 13, wherein a length of the stationary head 218 on one side of crossbar 214 is longer than the length of the other side of the crossbar. Provided in the stationary head 218 are a plurality of bores 222, preferably at least three, that penetrate the thickness of the stationary head 18 and accordingly have corresponding openings on the upper head surface 226 and the lower head surface 230. Note that the bores 222 are positioned at different vector offsets from the crossbar 214 along a length of the stationary head 18 in the directions of the double headed arrow 232. Further note the length of stationary head 218 is oriented substantially transversely to the length of crossbar 214 (e.g., in the direction of arrow 262). However, in an alternative embodiment the stationary head 218 is adjustable with respect to the crossbar 214; for example, the head 218 can be fixedly positioned at various angles with respect to the crossbar 214. Using appropriate pivoting mounting means, the head 218 can be adjusted so that it is fixed in a desired three-dimensional orientation, thus permitting a surgeon to create a desired surgical opening without being constrained to movement within fixed planes.

As shown in FIG. 11, each of the bores 222 has an interior surface with a plurality of notches 234 surrounding the interior of each bore 222 and extending at least partially through the bore. The notches 234 can be numerous in number (preferably at least 16) to facilitate various angular orientations of the grips 242 and 270 (see FIG. 11), but should number at least three.

A moveable retractor head 258 is operably connected to the crossbar 214 so that this head is moveable along the length of the crossbar (the movement as indicated by the double-headed arrow 262). The moveable retractor head 258 has at least one bore 224 that penetrates the moveable head 258. The bores 224 of the moveable retractor head 258 penetrate the moveable head in a similar manner to the bores 222 of the stationary head 218, and in one embodiment, bores 222 and 224 are substantially parallel. Additionally, the bores 224 also have notches 234 surrounding their interior surfaces (preferably at least 16 per bore) and extending at least partially through the thickness of the moveable head. Moreover, the bores 224 are also offset at various vectors (i.e., distances and/or directions) from the crossbar 214 along the length of the moveable head (i.e., the length being, again, in the directions of arrow 232).

The present invention further includes retractor levers 238 and 266 for maintaining a surgical opening or incision by contacting the sides of the opening. The retractor lever 238 includes an arm 246 having, at one end, a mating portion 250 with a substantially uniform cross-section with at least one edge, and preferably a plurality of edges 254 for mating into the notches 234 of any one of the bores 222. Additionally, the retractor lever 238 includes a grip 242 for gripping, for example, a rib and adjacent tissue when the retractor 210 is utilized in, for example, surgery wherein adjacent ribs are spread apart, as one skilled in the art will understand. Thus, the retractor lever 238 may be fitted into a suitable one of the bores 222 in the stationary head 218 as is described hereinbelow. The retractor lever 266 is similar to lever 238. That is, retractor lever 266 has the same functional components as lever 238. That is, the retractor-lever 266 has an arm 268, a mating portion 274 and a grip 270. Thus, a rib and tissue adjacent an incision can be gripped by grip 270 when the mating portion 274 of the lever arm 278 is inserted into one of the bores 224 of the moveable head 258.

The moveable head 258 is adjustable along the toothed crossbar 214 by a crank assembly 282 (whose external features are shown in FIG. 10 and whose internal cranking mechanism is conventional). Note that the external portions of the crank 282 provide for rotation of the crank cylinder 286 about the axis 290 as illustrated by the double-headed arrow 294. However, to assure that a surgeon can effectively rotate the crank cylinder 286 wherein there may be physical obstructions near the crank cylinder 286, an adjustable crank handle 294 is provided which is pivotally attached to the crank cylinder 286 so that the handle can be moved both about the crank cylinder 286 according to double-headed arrow 294 and also through any plane that also includes axis 290. Thus, the crank handle 298 moves in three dimensions and can be used to adjust the position of the moveable head 258 even when there are nearby obstructions.

By placing the retractor levers 238 and 266 in a bore 222 and 224 respectively of the stationary head 218 and the moveable head 258, respectively, adjacent ribs and surrounding tissue captured within the grips 242 and 270, respectively, can be separated when the moveable head 258 travels along the toothed crossbar 214 away from the stationary head 218. Further, since the mating portions 250 and 274 can have their respective edges 254 mated with notches 234 in any one of a number of orientations of their respective bores, the retractor levers can be configured in any one of a number of rotational positions about an axis (running lengthwise between the mating portion end and the grip end) of their respective arms. That is, the retractor levers 238 and 266 can be rotationally positioned according to double-headed arrows 302 and 306, respectively, and then fitted into respective bores 222 and 224. In one embodiment, the notches 234 are positioned within the bores 222 and 224 so that the retractor levers may be rotated in increments of 15.5 degrees through a complete circle, thereby allowing substantial reflexibility in conforming with a patient's anatomy. Further, since the mating portions 250 and 274 slide within the bores 222 and 224, different lengths (e.g., at least about 1 inch, more preferably about 3 inches and most preferably at least about 5 inches) of these mating portions may be provided within (or through) their respective bores so that the grips 242 and 270 may be at different lengths from the toothed crossbar 214. Accordingly, the sides of a surgical incision gripped by the grips 242 and 270 need not be directly opposite one another.

Thus, the present invention allows the grips 242 and 270 to be independently oriented in three dimensions (i.e., rotated in two dimensions about their corresponding arms and slidably offset from the toothed crossbar 214 in the third dimension) for customizing the fitting of the retractor 210 to the contour of a surgical patient's body and the incisions made on the patient during surgery. A surgeon is able to create a desired retraction of a surgical opening between adjacent tissues and/or bones. Thus, retraction using the present invention may include the following steps:

(a) determining a desired distance of each of the grips 242, 270 from the toothed crossbar 214;

(b) selecting a desired angle of the grips 242, 270, either prior to or after the grips have been inserted into the surgical incision site;

(c) inserting the mating portions 250, 274 into the respective toothed bores 222, 224; and (d) adjusting the distance between the stationary head 218 and the moveable retractor head 258.

Accordingly, performing the above steps with the retractor 210 facilitates access into relatively small openings by not only spreading apart surgical incision sides in one or two dimensions, as is possible with prior art, but also allows for a third dimensional adjustment. Thus, for example, a "tunnel-like" cavity can be created between a patient's ribs by retracting the ribs apart approximately 2 to 4 inches such that one rib is pushed down and another (e.g., adjacent) rib is raised up, while spreading the ribs apart laterally along a plane or contour of the patient's body.

Additionally, since the retractor levers 238 and 266 are removable, alternate retractor levers having different configurations of grips may also be used, thereby allowing the present invention to be tailored to both the body type and contours of a surgical patient and also to the type of surgical procedure being performed. In particular, substantially differently configured grips may be utilized depending upon patient's body contour, the amount of body fat on the patient, the size of the patient (e.g., adult versus child) and the surgical procedure being performed (e.g., cardiovascular versus thoracic). Moreover, the levers 238 and 266 can be either disposable (e.g., plastic), or non-disposable (e.g., stainless steel).

FIG. 12 illustrates the present invention wherein two adjacent ribs 310 and 314 are being separated by the retractor 210 of the present invention due to the movement of the moveable head 258 in the direction of vector 316. In particular, the present figure illustrates a particularly important aspect of the present invention in that by placing the retractor levers 238 and 266 into bores 222 and 224 at different distances from the toothed crossbar 214, the forces exerted upon the ribs 310 and 314 along the length of the toothed crossbar 214 (may be substantially different. Consider each of the force vectors 318 and 320 (these vectors being parallel to vector 316) exerted on the ribs 310 and 314, respectively, by the retractor 210. When these vectors are decomposed into force vectors relative to the axis 322 extending through the cross-sectional centers of the ribs 310 and 314, it can be seen that a component vector 326 corresponding to the force vector 318 forces the rib 310 downward (i.e., toward the patient's body) while a component vector 330, corresponding to the force vector 320, forces the rib 314 upward (i.e., away from the rest to the patient's body). Thus, assuming the axis 322 is substantially parallel to the contour of the patient's rib cage between ribs 310 and 314, the configuration of the present invention in FIG. 12 not only separates the ribs along the axis 322 but also separates the ribs by lifting one and depressing the other. Thus, for example, by using the retractor 210 in cardiovascular surgery, a surgical opening exposing the patient's heart can be maintained, for performing effective cardiovascular surgery through a tunnel provided to the heart. Thus, for bypass surgery, this gives good access for resection of the mammary artery, as one skilled in the art will understand.

Note that various alternative embodiments to the description of the embodiment above are also within the scope of the present invention. For example, the stationary head 218 may be replaceable so that different configurations of bores 222 are made available. Similarly, alternative moveable heads 258 having different bore 224 configurations may be utilized. Note that, for example, by changing the heads 218 and/or 258, at least the head sizes may be made appropriate to the size of the patient (i.e, potentially small heads for a small patient). Additionally, in another embodiment, the notches 234 within one or both of the bores 222 and/or 224 may be rotatable to anyone of a plurality positions within the bore(s) such that the rotatable notches may be fixed in a desired orientation by, for example, a locking and unlocking lever (not shown). Thus, if during a surgical procedure, where the grips 242 and 270 are gripping the sides of an incision and it becomes desirable to rotate one or both of the grips, then the bore(s) may be unlocked, rotated and then reallocate in a different position.

In another embodiment of the present invention, the crossbar 214 may be contoured along its length to conform to, for example, the contour(s) of a patient's body. Thus, the crossbar 214 may have an arcuate rather than a straight length.

In yet another embodiment, the stationary head 218 is rotatable at the attachment site with the crossbar 214 so that the bores can be rotated (about an axis, e.g., corresponding with the length of the crossbar 214) and locked to any one of a plurality of positions. For example, a separate crank (not shown) may be used for rotating the bores 222 while the retractor is in use, thereby providing a surgeon with the ability to adjust, e.g., the force vectors 326 and 330 without disengaging the retractor from the incision to make such adjustments.

Figure 15:
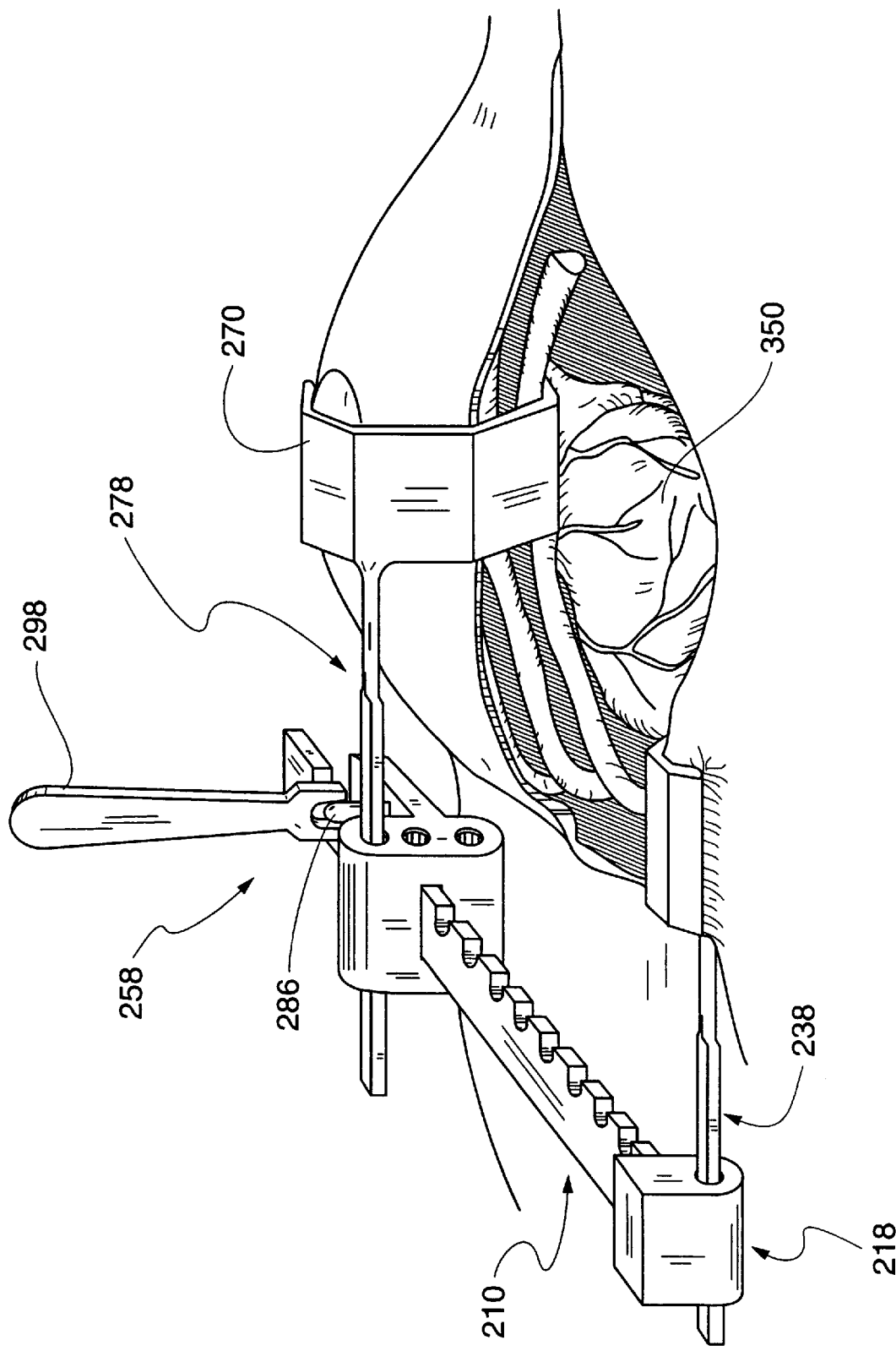
FIG. 15 illustrates one surgical technique for using the surgical retractor 210 for providing a tunnel or cavity to and above the heart such as may be desired for mammary artery resection.
Figure 16:
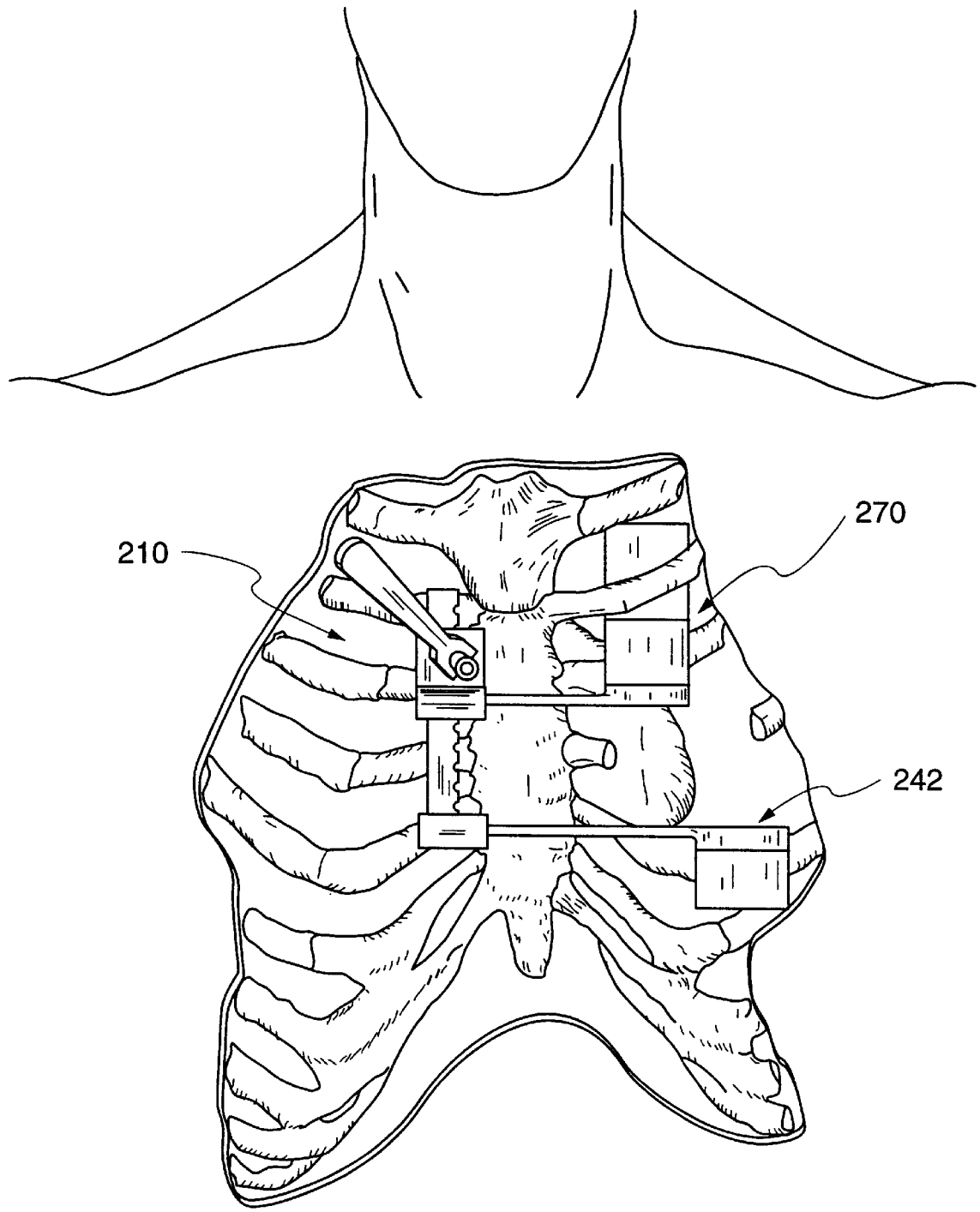
FIG. 16 is an elevational view corresponding with FIG. 15.
Figure 17:
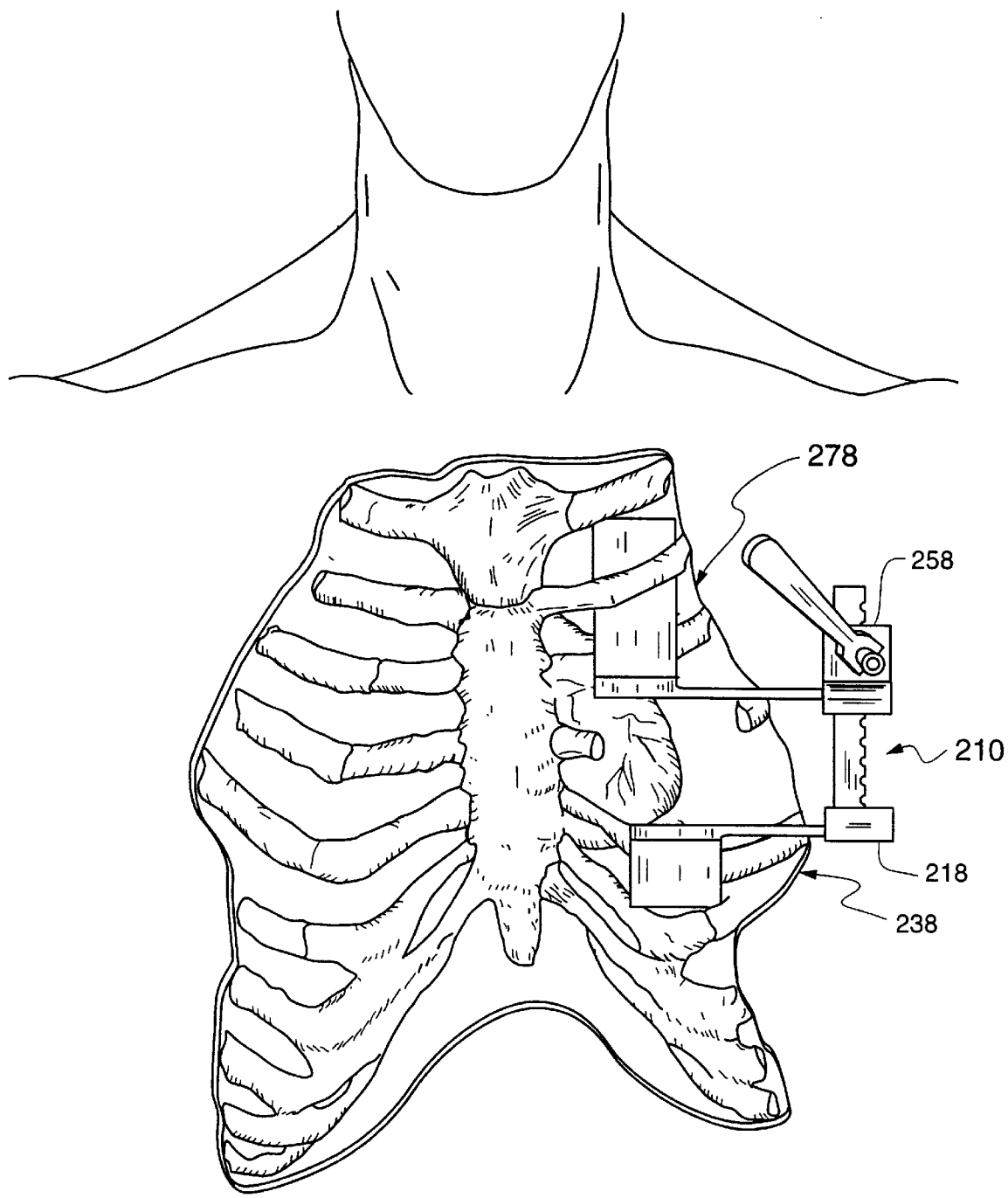
FIG. 17 shows the use of the surgical retractor 210 on an opposite side of the surgical incision.

Alternative embodiments of the surgical retractor 210 are provided in FIGS. 13 and 14. In the embodiment of FIG. 13, there is a single bore 224 in the moveable head 258. In the embodiment of FIG. 14, there is a single bore 222 in the stationary head 218 and a plurality of bores 224 in the moveable head 258. Further, note that in this latter embodiment, the crank cylinder 286 and the axis (of rotation) 290 are perpendicular the bores 222, 224 (instead of being parallel as in previous embodiments). Moreover, whereas in FIG. 12 the lifting of tissue about a surgical incision was described as occurring from a retractor lever 238 being placed in a bore 222 having the largest offset from the crossbar 214, and with the lever 238 being closer to the patient than where the crossbar joins the stationary head 218, in the present embodiment of FIG. 14, the surgical retractor 210 is used as shown in FIGS. 15, 16 and 17. That is, the bore 224*a* is positioned away from the patient and provided with a retractor lever such as 278 of FIG. 10 so that the extended or longest portion of the grip 270 is placed within the surgical opening. Thus, the grip 270 maintains an opening or tunnel extending both to the patient's heart 350 and above the heart towards the collar bone (preferably at least to the first rib), while a grip, such as grip 238 of FIG. 10, is provided within the stationary head 218 for exerting a downward pressure on the opposite side of the surgical incision. FIG. 16 shows an elevational view corresponding to FIG. 15 illustrating how access to both the patient's heart and the mammary artery above (or closer to the collar bone) is provided as one skilled in the art will understand. That is, a section of the fourth rib is removed and the grip 270 is inserted so that it extends to the second rib while the grip 242 grasps the fifth rib. In an alternative surgical technique, as shown in FIG. 17, the retractor 210 can be positioned on the opposite side of the patient to that of FIG. 16, wherein the retractor levers 278 and 238 are inserted into their corresponding bores from the opposite sides of the retractor 210. Further note that due to the small size of the retractor 210, it may be used on virtually all size patients, male and female.

In yet another embodiment of the surgical retractor 210, the bores 222 and 224 may be replaced with substantially universal lever fittings so that levers having a wide variety of configurations for the mating portions 250 and 275 can be utilized by the present embodiment.

When using the present invention, a surgeon selects retractor levers appropriate to the patient and the surgical procedure. Note that various embodiments of retractor levers may be used with the present invention. For example, both disposable and non-disposable levers may be used. Moreover, levers having a wide variety of grips can be incorporated into the present invention. For instance, grips having malleable or flexible fingers can be used, wherein the fingers are useful in, e.g., retracting fatty tissue from a surgical site. Accordingly, once the desired levers have been selected, the grips (e.g., 242 and 270) of the selected retractor levers may be inserted into an incision so that each grip grasps an opposite side of the incision. Subsequently, after orienting the grips within the incision and adjusting the spacing between the stationary head 218 and the moveable head 258 (typically so that the heads are adjacent one another), the corresponding mating portions of the retractor levers are inserted into appropriate bores within the stationary head 218 and the moveable head 258 so that the desired orientation of the grips is maintained. Following this, the surgeon can commence retracting the sides of the incision by rotating the crank assembly 282 until the desired incision opening is obtained.

Figure 20:
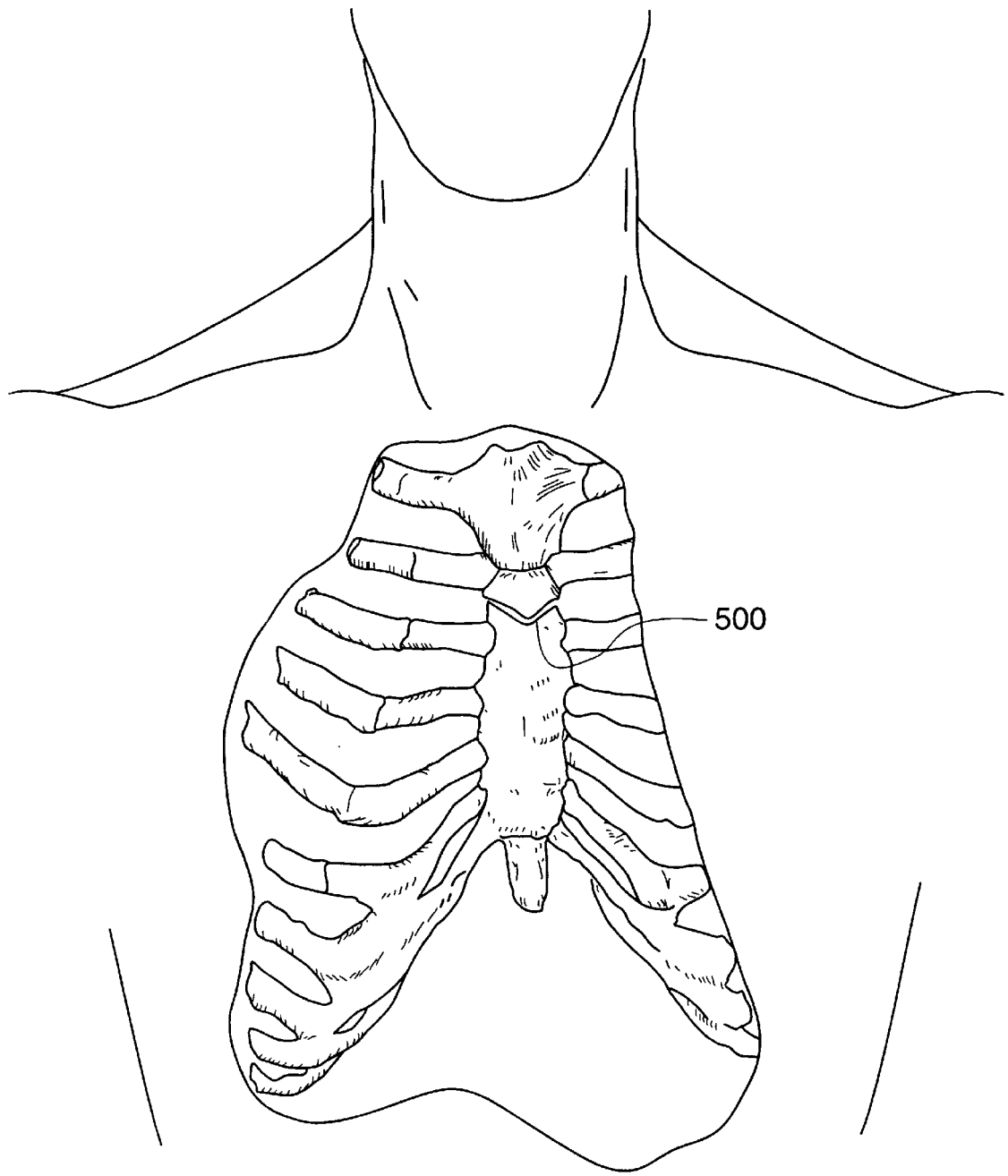
FIG. 20 illustrates the surgical incision made during a cardiac replacement surgery.
Figure 21:
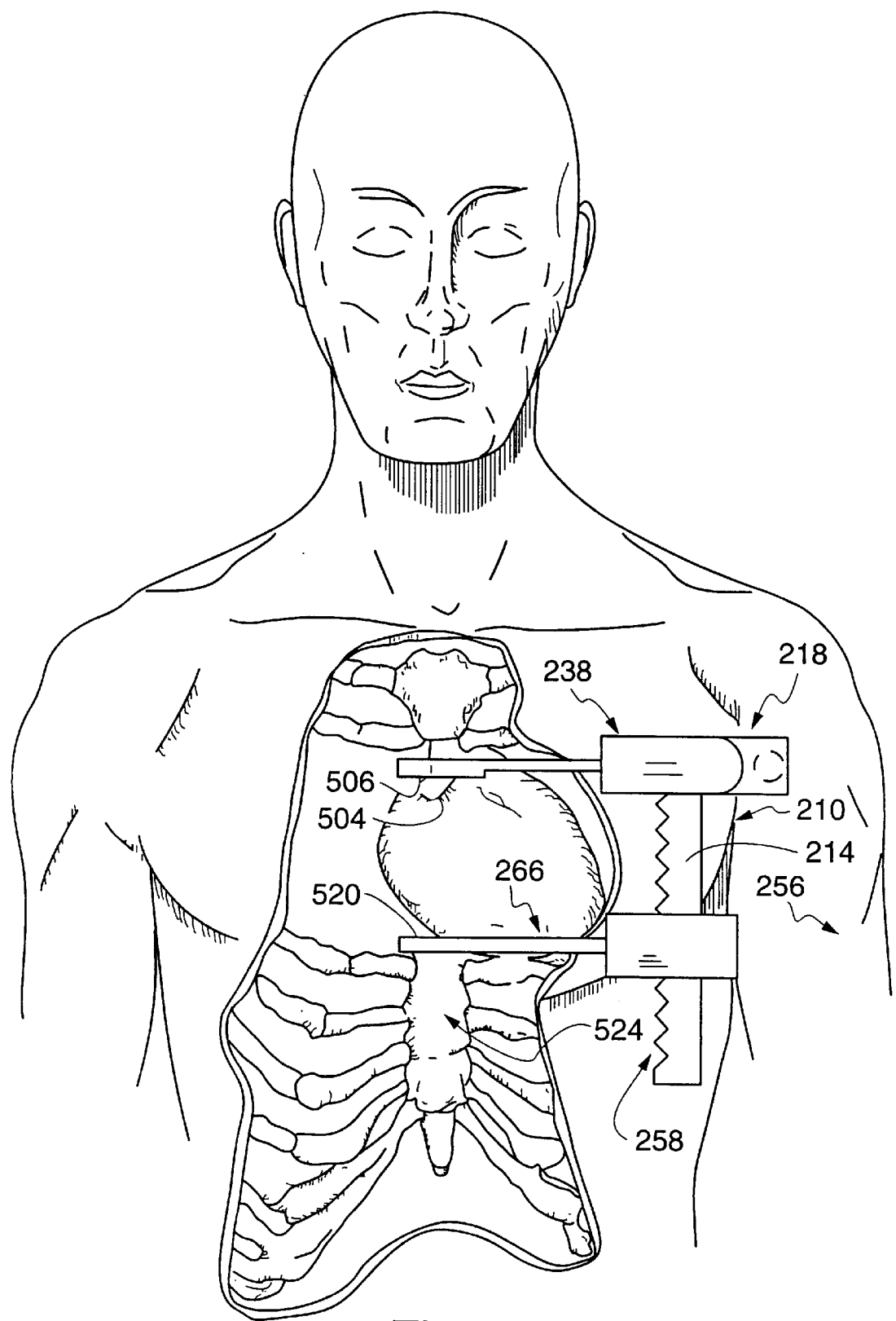
FIG. 21 illustrates the use of the retractor 210 provided in FIGS. 14, with the retractor levers of FIGS. 18 and 19 when performing valve replacement surgery.

Examples of alternative embodiments of retractor levers 238 and 266 are shown in FIGS. 18 and 19, respectively. The retractor levers of these figures are particularly useful when used together in, for example, cardiac valve replacement surgery, wherein these retractor levers are utilized in separating portions of a patient's sternum that has been surgically severed to gain access to the heart. To illustrate this, reference is additionally made to FIGS. 20 and 21. FIG. 20 shows the configuration of the cut 500 through a patient's sternum during a cardiac valve replacement surgery. FIG. 21 shows the retractor 210 (e.g., the embodiment of FIG. 14), wherein the retractor levers of FIGS. 18 and 19 are used during this surgery. In particular, the opening 508 of retractor lever 238 (FIG. 18) receives the point 506 of this upper "V", thereby assuring a secure and stable grip for retraction during the surgery. That is, since the opening 508 has a length 512 of about 2 cm and a width 516 of about 1.5 cm, the opening 504 surrounds a sufficiently large mass of the sternum so that for a typical adult it is very unlikely that the grip will accidentally disengage from the upper "V".

Referring now to FIGS. 19 and 21, the retractor lever 266 is positioned so that the opening 520 of grip 270 surrounds the entire sternum portion 524 (FIG. 21). That is, the grip retainers 528 (FIG. 19) retract against the tissue and ribs surrounding the sternum. Thus, during cardiac valve surgery, the sternum is severed, for example, between the second and third ribs and once the retractor levers 238 and 266 are fit to opposite sides of the sternum cut, the grips 242 and 270 are retracted so that grip 242 pushes toward the patient and grip 266 lifts away from the patient (i.e., the embodiment of FIG. 14 is used in FIG. 21 with the crank 286 pointing downward).

Note that as with grip 242, grip 270 is designed to securely and stably grip the ribs and tissue around the lower portion of the sternum.

In one method of use, after selecting the retractor levers and adjusting the spacing between the heads, the surgeon may insert the selected retractor levers into the surgical retractor bores at the desired orientations and then fit the grips onto opposite sides of the incision.

Of course, regardless of the order in fitting the retractors into the incision and the retractor bores, it is an important aspect of the present invention that the surgeon can easily reorient the retractor levers within the retractor heads. That is, since the mating portion of each retractor lever can be easily removed from a receiving bore (222 or 224), the surgeon can reposition a retractor lever within the receiving bore (and thereby change the position of the corresponding tissue grip), or the surgeon can remove the retractor lever from the receiving bore and place the lever's mating portion in an alternative bore within the same head (assuming this head includes at least two bores).

Further note that the present retractor may be used for other types of surgeries than keyhole or mini-surgeries. In particular, the present retractor may function as a more conventional retractor when the levers are not at different offsets from the crossbar 214. However, it is an aspect of the present invention that by displacing both levers the same (e.g., maximal) amount and direction from the crossbar 214, the crossbar can be displaced from the surgical site, thereby allowing better access to the surgical site.

The retractor levers described above are particularly useful for cardiac surgery such as valve or bypass surgery wherein the incision is retracted open substantially in a direction coincident with the length of the patient. That is, these retractor levers are particularly useful for spreading ribs and/or spreading portions of the sternum as discussed above.

Figure 27:
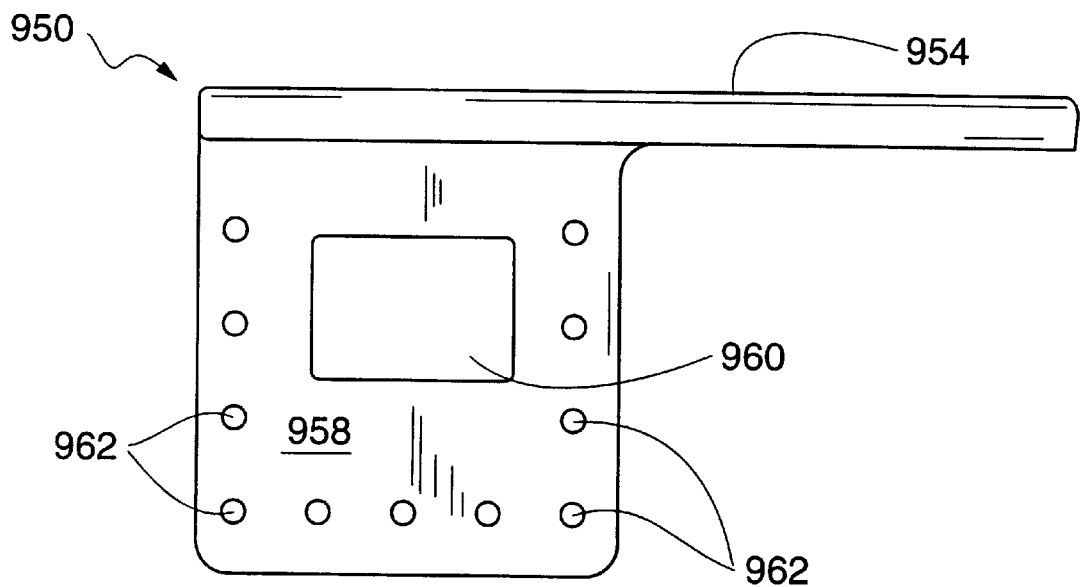
FIGS. 27 and 28 show views of an embodiment of a retractor lever 950 used particularly in mitral valve surgery.
Figure 28:
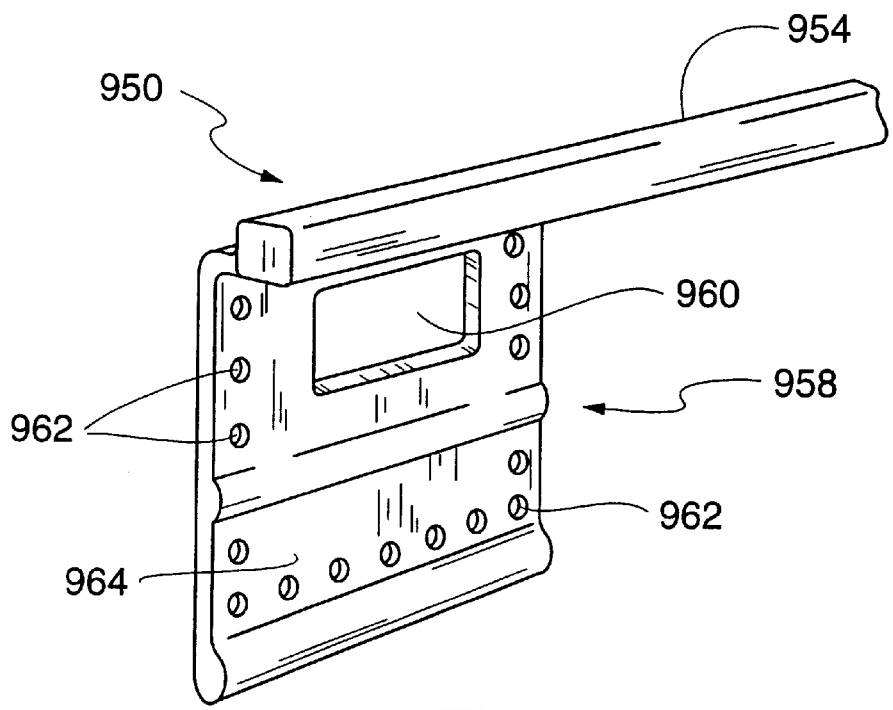

However, when cardiac surgery is performed wherein an incision is retracted open in a direction substantially across or traverse to the length of the patient, then the retractor lever 450 of FIGS. 27 and 28 may be used. Where such traverse retraction is desired (typically on the patient's right side), surgery may include the removal of at least a portion of a rib in order to obtain adequate heart access (e.g., when performing mitral valve surgery). However, it can be that the patient's right lung will obscure or reduce access to the heart in that the lung will tend to extend into the retracted surgical opening. Accordingly, the retractor lever 950 is useful for restricting the lung from entering the retracted opening. However, before further discussing the use of retractor lever 950, its structure will first be described. Accordingly, the retractor lever 950 includes a lever arm 954 that is shaped, and has a functionality substantially identical to the retractor lever arms shown in FIGS. 10, 18 and 19. Attached to one end of the lever arm 954 is a retractor grip 958. In one embodiment, the grip 958 extends from the lever arm 954 approximately 6.2 cm. The grip 958 has a large rectangular opening 960 for suturing through and around, when suturing tissue to the grip 958 as discussed hereinbelow. Additionally, the grip 958 includes a plurality of holes 962 substantially about the periphery of the grip, these holes being, e.g., 0.32 cm.

When using the retractor lever 950 for lung retainment as discussed above, the grip 958 is placed in one side of an incision while a grip of another of the retractor levers (e.g., lever 238, FIG. 10) is placed in an opposite side of the incision. More precisely, the levers are positioned so that the length of their corresponding arms extend substantially in the direction of the length of the patient, and the grips are inserted into the incision so that the surface 964 (FIG. 28) faces away from the other grip and toward the patient's right lung. Given that the arms of the retractor levers are inserted into the retractor 210, during retraction the surface area of grip 958 serves to both extend the incision opening to the heart and to block the right lung from entering the opening. Moreover, the surgeon may use the holes 462 and the opening 460 to temporarily suture the lung to the grip 958 to further block the lung from obscuring or blocking the incision opening. Note, however, the retractor lever 950 may have various other embodiments; e.g., instead of holes 962, hooked portions may be provided to which the lung may be sutured.

Figure 22:
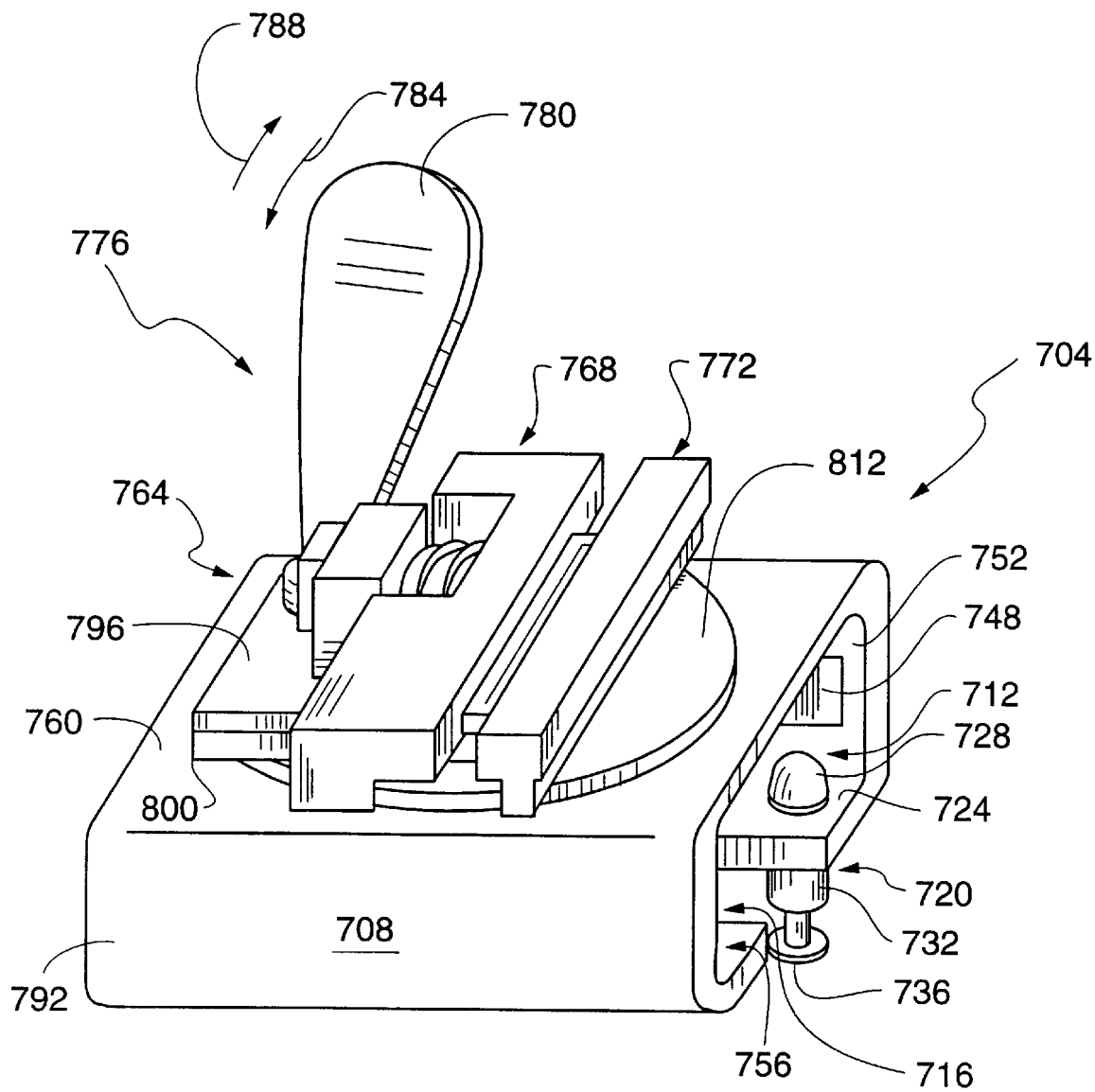
FIG. 22 shows an embodiment of a holder 704 for a shaft 90 of a heart dampening device, wherein the holder can be attached to a surgical retractor such as the surgical retractor 210.
Figure 23:
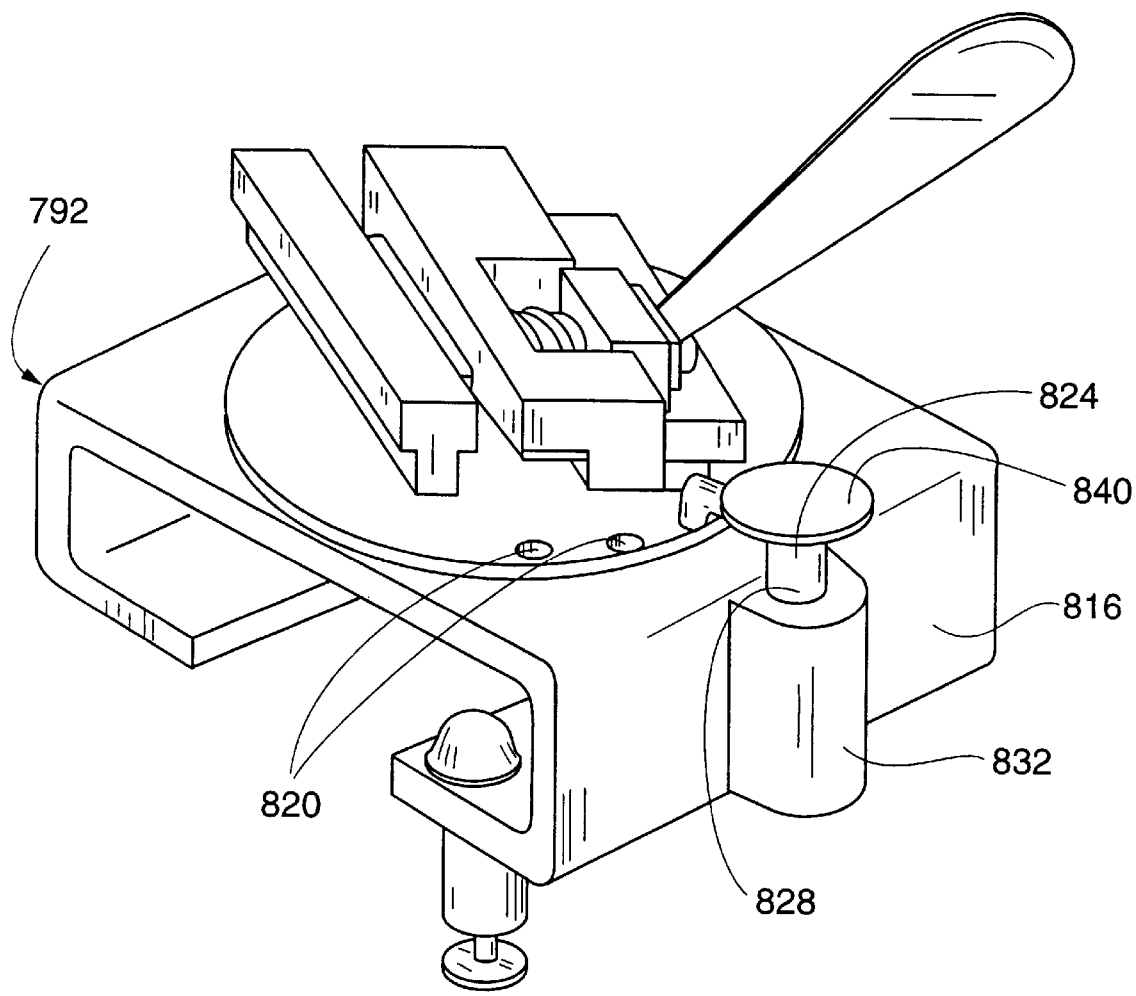
FIG. 23 shows a perspective view of the heart dampening device holder 704 of FIG. 22, wherein the side hidden in FIG. 22 is illustrated in this figure.
Figure 24:
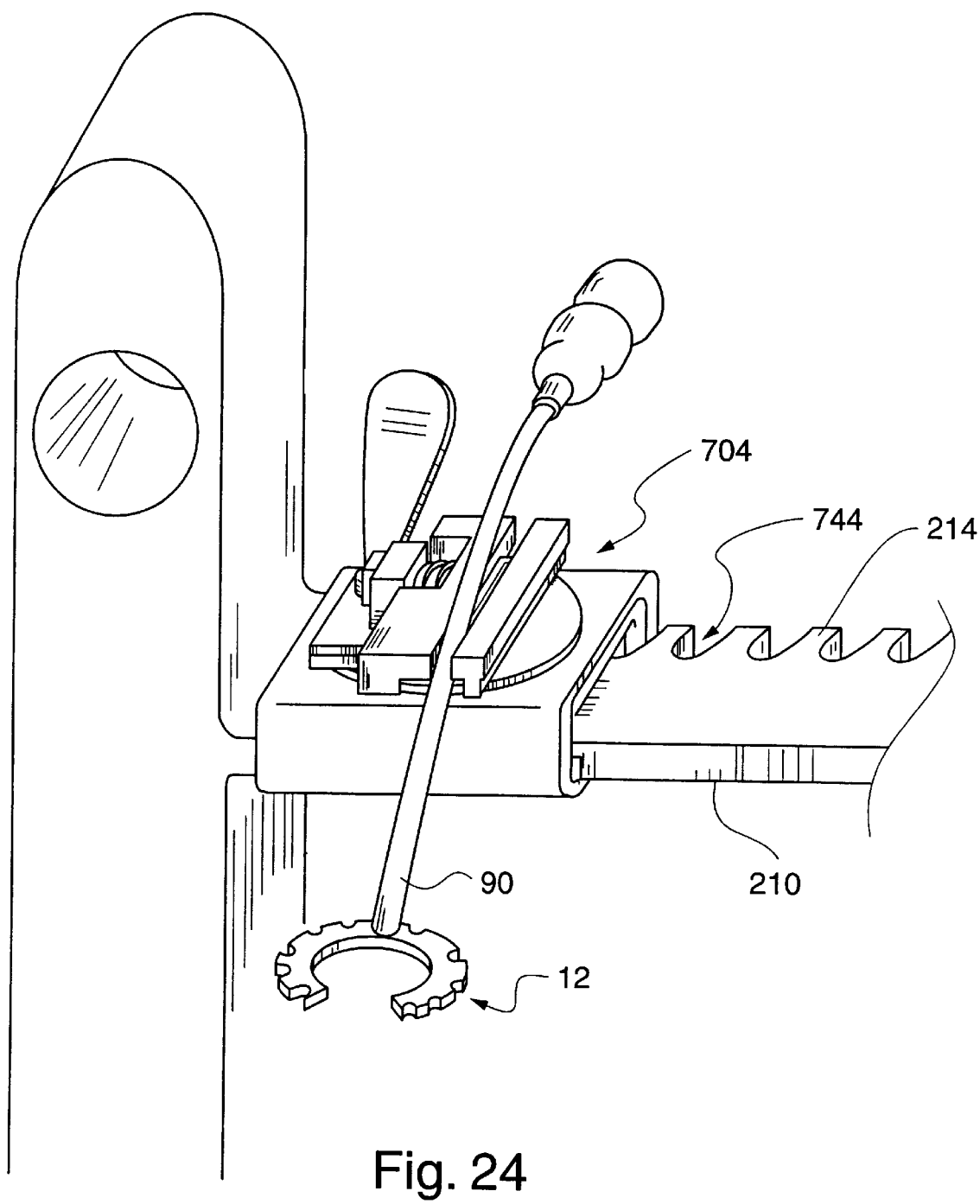
FIG. 24 illustrates the embodiment of the holder 704 from FIG. 22 attached to the surgical retractor 210.

FIGS. 22, 23 and 24 illustrate a first embodiment of a holder 704 for holding a shaft 90 of an embodiment of the device 10 of the present invention. The holder 704 includes an attachment housing 708 for attaching to a surgical retractor as, for example, is illustrated in FIG. 24. The attachment housing 708 has an interior chamber 712 for receiving the crossbar 214 through the receiving opening 716 that provides access to the interior chamber 712. A stop pin assembly 720 is attached to wall 724 of the attachment housing 708. The stop pin assembly 720 includes a spring biased stop pin 728 that protrudes partially into the interior chamber 712. The stop pin 728 is retractable into the stop pin casing 732 that is fixedly attached to the wall 724 so that the stop pin casing does not protrude into the interior chamber 712. Further, within the stop pin casing 732 is a spring (not shown) that biases the stop pin 728 towards the interior chamber 712. However, attached to a portion of the stop pin 728 within the stop pin casing 732 and protruding through an opposite end of the stop pin casing from the opening into the interior chamber 712 is a stop pin retractor 736 such that when the stop pin retractor is manually pulled in the direction of arrow 740, the stop pin 728 retracts from the interior chamber 712 and the holder 704 can be shifted along the crossbar 214. Subsequently, when the stop pin retractor 732 is released, the stop pin 728 locks the holder 704 into place by entering a tooth recess 744 of the crossbar 214.

Additionally, also provided within the interior chamber 712 is a leaf spring 748 that is attached to the wall 752 of the attachment housing. The leaf spring 748 is biased to extend into the interior chamber 712 so that when the holder 704 is provided on the crossbar 214, the leaf spring pushes against the teeth of the crossbar 214 so that the crossbar is held firmly against the interior walls of the L-portion 756. Accordingly, the stop pin assembly 720 and the leaf spring 748 together with the configuration of the inner chamber 712 allow the holder 704 to be firmly secured to the crossbar 214, and when desired, also allow the holder to be shifted along the crossbar as desired.

On the outer base surface 760 of the attachment housing 708, a clamp assembly 764 is provided, wherein this assembly is used to clamp and firmly hold the shaft 90 of a heart dampening device 10. The clamp assembly 764 includes a pair of clamping components 768 and 772, wherein the shaft 90 is held firmly in place when these two components are biased toward one another by the clamp activation subassembly 776. That is, the clamp activation subassembly 776 causes the clamping component 768 to move toward or away from the clamping component 772 depending on the movement of the lever 780. In the present embodiment, by rotating the free end of the lever 780 in the direction of arrow 784, the clamping component 768 moves toward the clamping component 772 for holding the shaft 90 in a desired position and orientation. Conversely, by moving the free end of the lever 780 in the direction of arrow 788, the clamping component 768 moves away from the clamping component 772.

One skilled in the art will appreciate that there are various embodiments for the clamp assembly 764. However, the embodiment in FIGS. 22, 23 and 24 includes a number of features that are particularly useful during a cardiac surgical procedure. For example, the clamping components 768 and 772 extend beyond the attachment housing exterior surface 792 so that the shaft 90 can be more easily grasped between the clamping components. Further, there is a clamp platform 796 to which the clamp activation subassembly 776 is fixedly attached and to which the clamping component 768 is slidably connected via the sliding of the end slots 804 about the overhang 800. However, note that the overhang 800 does not extend into the opening between the clamping components 768 and 772. Thus, this allows for additional flexibility by the surgeon in orienting the shaft 90 between the clamping components. Moreover, the clamp activation subassembly 776 is designed for both rapid clamping and declamping of the shaft 90. That is, the lever 780 moves the clamping component 768 between a position furthest away from the clamping component 772 and a closed position wherein the clamping components are adjacent one another by at most the lever having its free end rotate through an arc of 180°, wherein at the extreme open and closed positions of the clamping components the lever is substantially parallel to the clamp platform 796.

To enhance the versatility of the clamp assembly 764 further, this assembly is attached to the attachment housing via a swivel base 812 so that the entire clamp assembly 764 may be rotated about an axis that is perpendicular to the base surface 760 and includes the center point of the substantially circular swivel base.

However, it is also a feature of the holder 704 that the clamp platform 796 and the clamp activation subassembly 776 may be prevented from swiveling by a pin and slot configuration on the opposite side 816 from that of side 792 (as best shown in FIG. 23). In particular, this pin and slot configuration includes: (a) slots 820 that extend at least partially around the rim of the swivel base 812, and (b) a pin 824 having a bent offset 836 whose downwardly-turned free end has, e.g., a knob that may be aligned with and inserted into one of the slots 820 for anchoring the swivel base 812 in a desired orientation. In the embodiment of FIG. 23, the pin 824 has a shaft 828 that is slidable for moving in and out of a shaft housing 832. However, the shaft 828 and the shaft housing 832 mate in such a manner that the shaft does not rotate within the shaft housing. Additionally, the shaft housing 832 is internally configured (not shown) so as to also house a compression spring that biases the shaft 828 into the shaft housing to as great an extent as possible. Further, the pin 824 also includes a pinhead 840 that is of sufficient size and shape so that it can be easily manually grasped for extending the pin shaft 828 from the shaft housing 832 and releasing the knob of the bent offset 836 from any mating slot 820, thereby allowing the clamp assembly 764 to be rotated on the swivel base 812.

Accordingly, to use the holder 704, a surgeon or other surgical personnel slides the holder onto the crossbar 214 via the receiving opening 716. Subsequently, the holder 704 may be slidably positioned on the crossbar 214 by manually pulling the stop pin retractor 736 so that the stop pin 728 recedes from the interior chamber 712 and thereby allows the holder to slide across the crossbar. Upon positioning the holder upon the crossbar 214 and releasing the stop pin retractor 736 so that the stop pin 728 enters one of the tooth recesses 744, the clamp assembly 764 can then be rotationally positioned and fixed in place by pulling the pin 824 from its shaft housing 832 so that the clamp assembly 764 can be freely rotated. Assuming that the clamp assembly 764 has been fixed into place via the mating of the knob of the bent offset 836 with one of the slots 820, the shaft 90 of a heart motion dampening device 10 can be provided between the clamping components 768 and 772. Accordingly, by a half-turn of the lever 780, the clamping components 768 and 772 firmly grip the shaft 90 and thereby can maintain the ring-like structure 12 in a desired position upon the heart of the patient. Moreover, it is worthwhile to note that the holder 704 can be easily repositioned if necessary during surgery. Also, the combination of the heart dampening device 10 and the holder 704 can be easily and quickly discarded if an emergency situation occurs wherein alternative surgical procedures need to be immediately performed on the patient.

Figure 25:
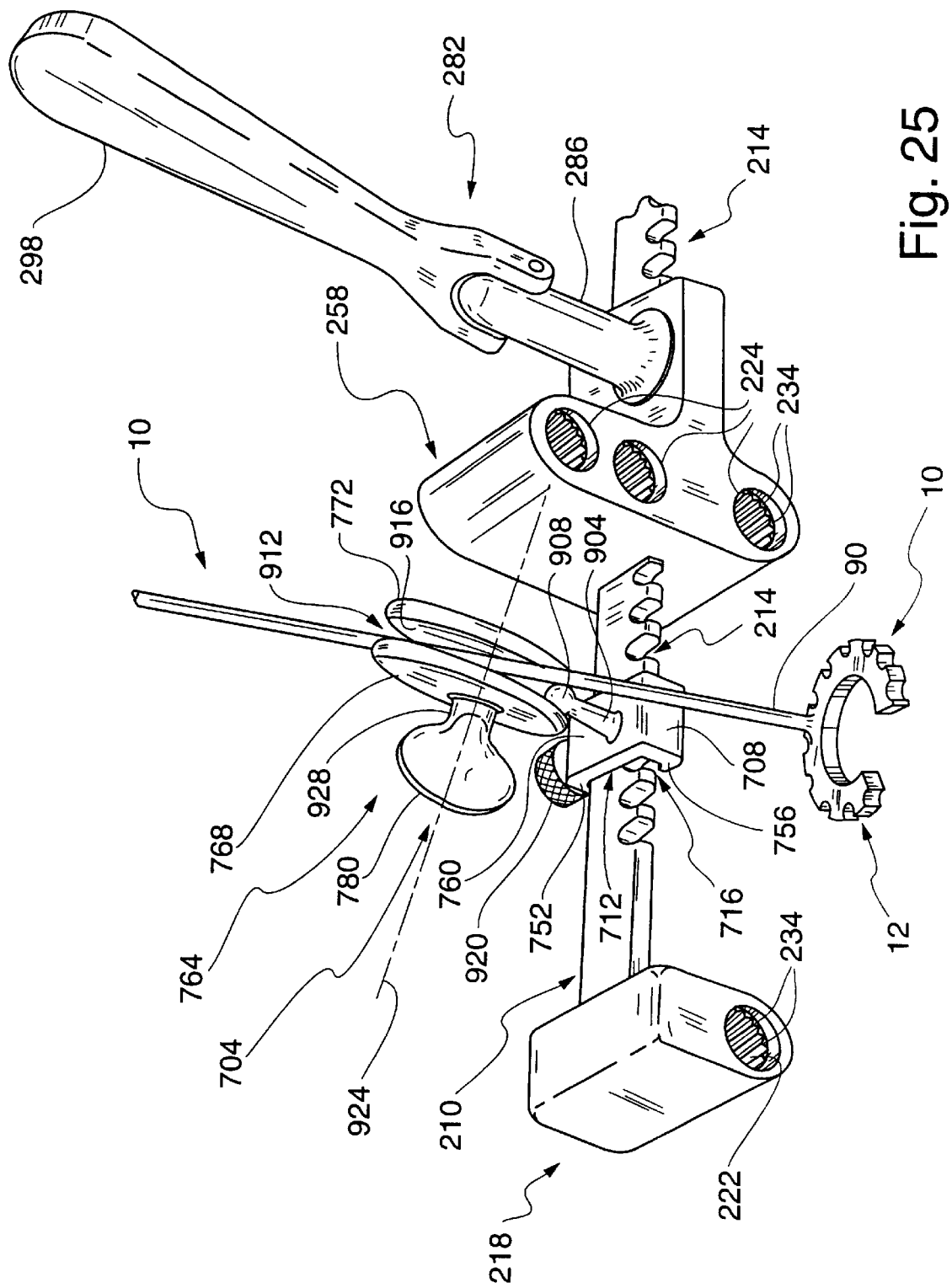
FIG. 25 illustrates a second embodiment of the holder 704 attached to an embodiment of the surgical retractor 210.
Figure 26A:
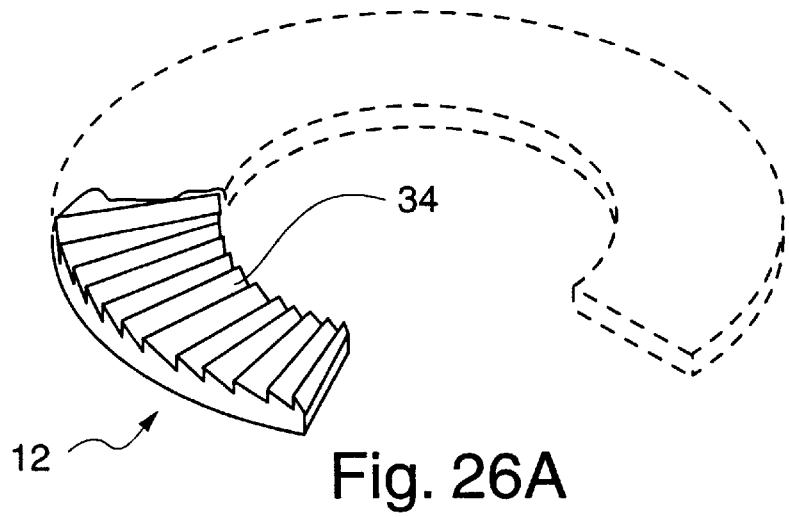
FIGS. 26A–26F illustrate various contours, serrations, and edges for anchoring the heart stabilization device 10 to the heart.
Figure 26B:
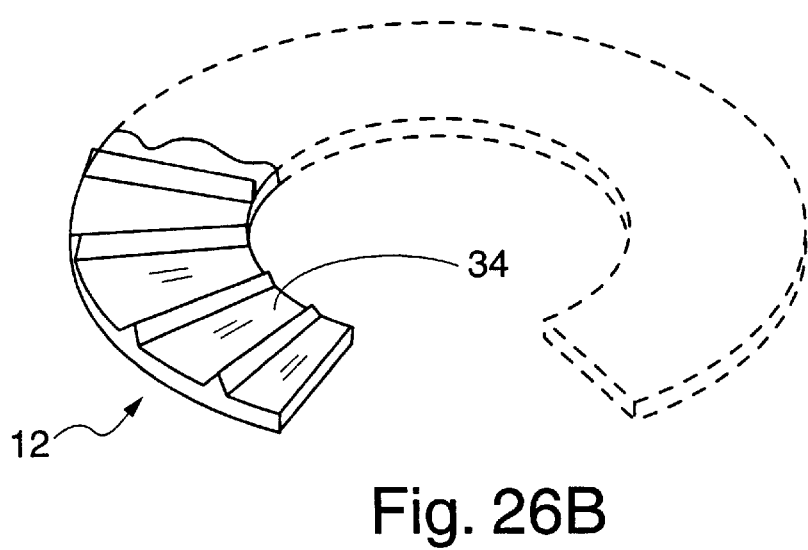
Figure 26C:
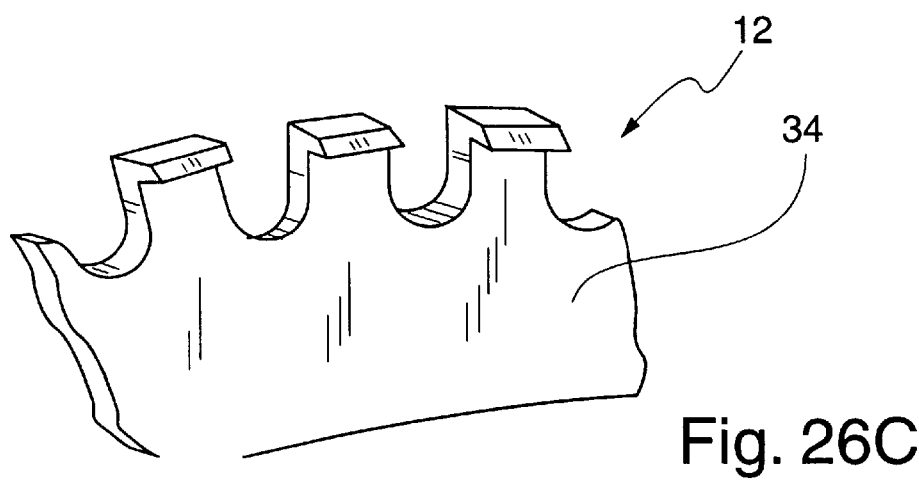
Figure 26E:
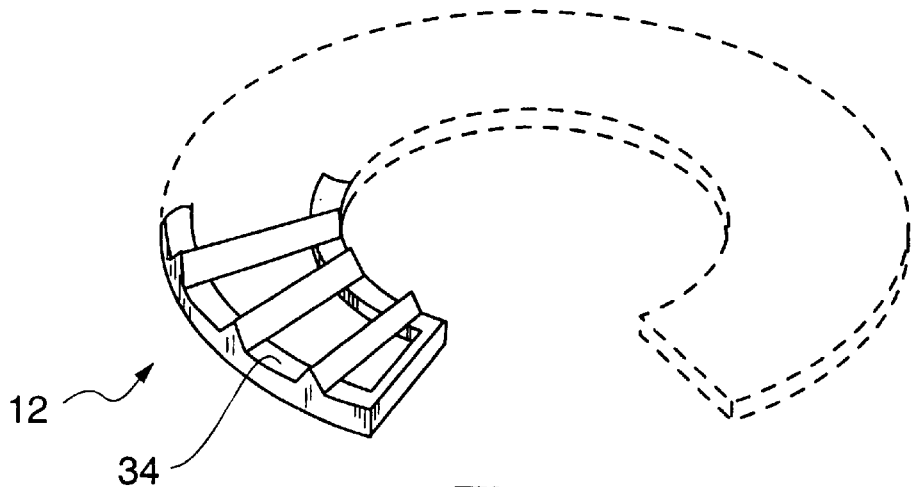
Figure 26D:
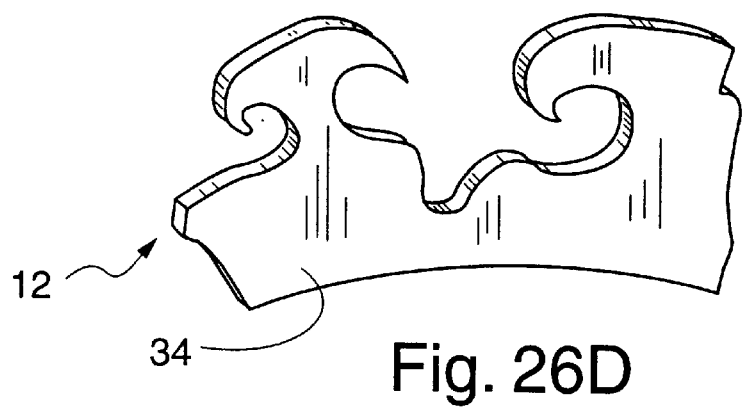
Figure 26F:
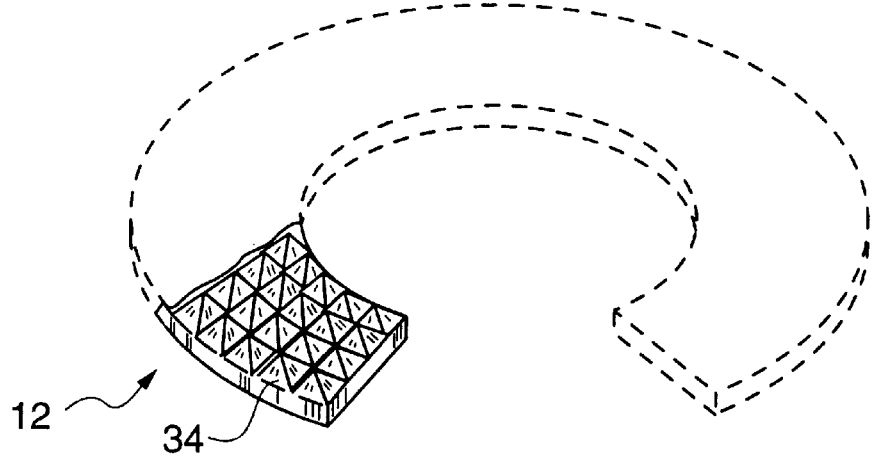

An alternative embodiment of the holder 704 is shown in FIG. 25. In particular, this embodiment of the holder 704 is also shown attached to an embodiment of the retractor 210, wherein this embodiment of the retractor is substantially similar to the embodiment of FIG. 14. Accordingly, to simplify the description of this figure, components of both the holder 704 and the retractor 210 having similar functionality to corresponding components described in previous figures, are provided with identical labels. Thus, referring particularly to the holder 704, the following components as discussed in the context of FIGS. 22–24, have a corresponding functionality and configuration: attachment housing 708, interior chamber 712, receiving opening 716, wall 724 (not shown), wall 752, L-portion 756, base surface 760, clamp assembly 764, clamping components 768 and 772, and lever 780. In addition, the present embodiment of the holder 704 has a support pedestal 904 projecting outwardly from the base surface 760, wherein the end of the support pedestal not attached to the base surface terminates in a pivot ball 908. The pivot ball 908 is seated within mating depressions (not shown) of the interior clamping surfaces 912 and 916 provided on the clamping components 768 and 772, respectively. Accordingly, the pivot ball 908 and the depressions on the interior clamping surfaces 912 and 916 are appropriately sized so that the clamping components 768 and 772 can both hold the shaft 90 and the clamp assembly 764 in desired positions when the two clamping components are tightened together, as will be explained hereinbelow. Additionally, the holder 704 also includes a threaded securing bolt 920 that is received into a mating threaded bore (not shown) in wall 752. The threaded securing bolt 920 is thereby used for securing the holder 704 to the crossbar 214, as one skilled in the art will understand.

In operation, the holder 704 of FIG. 25 is placed on the crossbar 714 and secured thereto by threading the threaded securing bolt 920 through the mating threaded bore in wall 752 so that the threaded end of the bolt 920 contacts the crossbar 214 and secures the attachment housing 708 so that it cannot slide along the length of the crossbar. Subsequently, if necessary, the lever 780 can be twisted about its axis 924 for adjusting both the orientation of the clamp assembly 764 in relation to the pivot ball 908, and in addition, adjusting the orientation of the shaft between the clamping components 768 and 772. That is, the lever 780 is integral with a shaft 928 that extends between the clamping components 768 and 772 and that is threaded for compressing the clamping components together when the lever 780 is twisted in a first direction and moves the clamping components away from one another when the lever is twisted in an opposite direction. Moreover, since the seating of the pivot ball 908 in the mating depressions of the interior clamping surfaces 912 and 916 provide a distance between these clamping surfaces slightly larger than the diameter of the shaft 90, the clamp assembly 764 can be oriented on the pivot ball by mildly tightening the lever 780 so that the shaft 90 is only loosely held between the interior clamping surfaces, and therefore, the heart dampening device 10 can be easily adjusted without disturbing the orientation of the clamp assembly 764. Subsequently, once both the clamp assembly 764 and the heart dampening device 10 are oriented as desired, the lever 780 may be further twisted to tighten the clamping components 768 and 772 together for firmly holding both the pivot ball 908 and the shaft 90.

Note that either holder embodiment 704 may also be used for holding other surgical devices besides the shaft 90 of a heart dampening device 10. For example, such holders may be used for holding lights, surgical clamps, surgical tubing, or any other surgical device that has a relatively narrow portion that can be fitted between the clamping components 768 and 772. Moreover, note that it is within the scope of the present invention that multiple clamping assemblies 764 may be provided on the crossbar 214 simultaneously. Additionally, embodiments of the holder 704 may be provided that also attache to the stationary head 218 and/or the moveable retractor head 258. In particular, by providing, e.g., grooves on the external surfaces of the heads 218 and/or 258, holders similar to holders 804 may be secured to one or both of heads 218 and 258.

The foregoing discussion of the invention has been presented for purposes of illustration and description. Further, the description is not intended to limit the invention to the form disclosed herein. Consequently, variation and modification commiserate with the above teachings, within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A method for dampening heart motion during a surgical procedure comprising:

positioning a ring-like structure having one or more flanges protecting therefrom in a particular position so that a first surface of the ring-like structure contacts the beating heart, wherein an interior opening of the ring-like structure allows surgical access to a desired surgical site;

applying a force to the ring-like structure so that a plurality of heart tissue engaging projections penetrate the surface of the heart tissue for anchoring the ring-like structure to the beating heart;

applying a motion dampening resistance to the ring-like structure so that the first surface remains in contact with the heart during an access to the surgical site, wherein the resistance is transmitted to the heart through the tissue engaging projections, said resistance applied through said one or more flanges.

2. A method as claimed in claim 1, wherein said step of applying the motion dampening resistance includes transferring the resistance to the ring-like structure via one or more hold down attachments projecting from the ring-like structure.

3. A method as claimed in claim 1, wherein said step of positioning includes attaching the ring-like structure to a surgical retractor attachment assembly, so that the application of the motion dampening resistance is at least in part due to the retractor attachment assembly pressing the ring-like structure against the beating heart.

4. An apparatus for dampening heart motion during a surgical procedure, comprising:

a ring-like structure having a first and second surface, said first surface for placing in contact with the heart and the second surface facing away from the heart, wherein said structure also has an interior opening for accessing a surgical site on a beating heart;

a plurality of heart tissue engaging prongs attached to said structure, wherein a point from each prong is directed substantially toward the heart when the first surface is in contact with the heart;

a hold down attachment means for applying a pressure for maintaining the first surface against the heart, said hold down attachment means includes one or more flanges projecting from the ring-like structure for holding the first surface against the heart.

5. An apparatus as claimed in claim 4, wherein said one or more flanges each attach to said second surface.

6. An apparatus as claimed in claim 4, wherein said one or more flanges each are operably attached to a surgical retractor for applying a force for anchoring the first surface to the beating heart.

7. An apparatus as claimed in claim 4, wherein said structure substantially surrounds the surgical site.

8. An apparatus as claimed in claim 4, wherein said structure does not entirely surround the interior opening.

9. An apparatus as claimed in claim 4, wherein said structure has a thickness between said first and second surfaces of less than two millimeters.

10. An apparatus as claimed in claim 4, wherein at least one of said tissue engaging prongs is attached to said structure substantially at an outer perimeter of said structure.

11. An apparatus as claimed in claim 4, wherein at least one of said heart tissue engaging prongs is attached to said structure substantially at an inner boundary of said ring-like structure defining the interior opening.

12. An apparatus as claimed in claim 4, wherein at least one of said heart tissue engaging prongs projects substantially away from the first surface.

13. An apparatus for dampening heart motion during a surgical procedure, comprising:

a structure having a first and second surface, said first surface for placing in contact with the heart and the second surface facing away from the heart, wherein said structure also has an interior opening for accessing a surgical site on a beating heart;

a plurality of heart tissue engaging prongs attached to said structure, wherein a point from each prong is directed substantially toward the heart when the first surface is in contact with the heart; and an additional component for dampening the motion of the beating heart, said additional component operably attached to said structure and substantially surrounding said structure.

14. An apparatus as claimed in claim 13, wherein said additional component contacts the heart with a motion dampening material.

15. An apparatus as claimed in claim 13, wherein said motion dampening material includes one of an elastic composition and a foam gel for at least partially dampening the heart motion.

* * * * *